US007803635B1

(12) United States Patent
Meece

(10) Patent No.: US 7,803,635 B1
(45) Date of Patent: Sep. 28, 2010

(54) PURGE AND TRAP CONCENTRATOR WITH SPARGE VESSEL

(75) Inventor: Douglas A. Meece, West Chester, OH (US)

(73) Assignee: EST Analytical, Inc, Fairfield, OH (US)

( * ) Notice: Subject to any disclaimer, the term of this patent is extended or adjusted under 35 U.S.C. 154(b) by 304 days.

(21) Appl. No.: 12/037,977

(22) Filed: Feb. 27, 2008

(51) Int. Cl.
*G01N 1/22* (2006.01)
(52) U.S. Cl. .................. 436/181; 436/54; 436/174; 422/68.1; 422/83; 422/89; 73/23.2; 73/23.35; 73/23.41; 73/23.42
(58) Field of Classification Search ............. 436/181, 436/54, 174; 422/68.1, 83, 89; 73/23.2, 73/23.35, 23.41, 23.42
See application file for complete search history.

(56) References Cited

U.S. PATENT DOCUMENTS

| 5,337,619 | A | 8/1994 | Hodgins et al. |
| 5,441,700 | A | 8/1995 | Markelov |
| 5,827,944 | A | 10/1998 | Nickerson |
| 5,866,072 | A | 2/1999 | Bowe, Jr. et al. |
| 5,932,482 | A | 8/1999 | Markelov |
| 6,146,895 | A | 11/2000 | Green et al. |
| 6,277,649 | B1 | 8/2001 | Markelov |
| 6,365,107 | B1 | 4/2002 | Markelov et al. |
| 6,395,229 | B1 | 5/2002 | Markelov |
| 6,395,560 | B1 | 5/2002 | Markelov |
| 2004/0142481 | A1* | 7/2004 | Hartlein ..................... 436/164 |

* cited by examiner

*Primary Examiner*—Robert J Hill, Jr.
*Assistant Examiner*—Dwan A Gerido, Ph.D.
(74) *Attorney, Agent, or Firm*—Frederick H. Gribbell

(57) ABSTRACT

A purge and trap concentrator system that includes a sparge vessel, and includes a variable gas flow valve for controlling the gas pressure in an analytic trap or the sparge vessel; a sensor that detects both a foaming sample state and a high liquid level in the sparge vessel, using one optical sensor; a control scheme that re-directs the purge gases to a second inlet of the sparge vessel during a foaming condition; a control scheme that uses a split flow to enhance the quantity of sample gases passed from an analytic trap; an electrically powered thermal energy source with a fan raising the sparge vessel temperature via thermal convection.

16 Claims, 12 Drawing Sheets

PURGE AND TRAP CONCENTRATOR WITH SPARGE VESSEL

BACKGROUND OF THE INVENTION

1. Field of the Invention

The present invention relates to purge and trap concentrator systems, and, more particularly, to those that include a sparge vessel. The invention, in various embodiments, includes: (1) a variable gas flow valve for controlling the gas pressure in the sparge vessel, or in an analytic trap; (2) a foam sensor subassembly that detects both a foaming sample state and a high liquid level in the sparge vessel, using a single optical sensor; (3) a control scheme in which a purge and sampling procedure can continue after a foaming sample has been detected, by re-directing the purge gases to a second inlet of the sparge vessel; (4) a control scheme in which a desorbtion mode uses a split flow to enhance the quantity of sample gases that are passed to an analyzer instrument from an analytic trap; (5) a thermal heater subassembly that uses an electrically powered thermal energy source and a fan to raise the temperature of the sparge vessel via thermal convection during a bake mode, by directing heated air to the sparge vessel using a ductwork arrangement with the fan; and (6) a desorbtion pressure control mode in which the pressure at an analytic trap is brought to a controlled value that will allow the system to jump to the inject mode without undergoing a pressure surge at the trap.

2. Description of the Related Art

Purge and trap concentrators have been is used to extract VOCs from aqueous samples, or from a solid sample matrix. In many systems, a sample is housed in a sealed vessel known as a sparge vessel. The sparge vessel typically is constructed in a U-shape design with an inlet side (purge portion) and an outlet side (sample portion). An inert gas (purge gas) of helium or nitrogen sweeps the aqueous sample at a controlled flow rate known as purging. The purge gas is introduced on the purge portion of the sparge vessel; typically the purge gas stream passes through a frit placed in the bottom of the sample portion of the sparge vessel. The frit disperses the gas into many fine streams to increase surface contact of the gas with the sample for extraction of VOCs. One problem with purging aqueous samples is they have a tendency to foam, and if the foam is left unattended the sample could come in contact with internal pathway components of the instruments pathway causing contamination to the entire system. This can require costly repairs and downtime for the testing laboratory, along with rendering the analytical test data invalid.

Today most purge and trap concentrators have a foam detection sensor that will turn off the purge gas and stop the sampling process, or continue in a "safe mode" to prevent costly repairs. The problem here is that the sample is then wasted and deemed unusable. The laboratory will have to re-run the sample (if it has one) or contact the client to send a new sample.

One approach to this problem is pre-treating suspect samples with an anti-foaming agent, such as Dow Corning Silicone RID emulsion. However this treatment can raise concerns regarding the sample integrity. A second approach is to disrupt the foam with a heat source to continue the analysis. However the heating of the foam and headspace of the sample containing extracted VOCs could also raise some questions on the integrity of the extracted VOCs.

Most purge and trap concentrators using a sparge vessel provide an inert (purge) gas that is swept through the concentrated chemical sample at a controlled flow rate, thereby extracting the VOCs from the sample. The extracted VOCs are then placed in fluidic communication with an adsorbent trap for concentrating. The adsorbent trap is thermally heated to release the extracted VOCs from the adsorbent bed of the trap. A second passage of inert (carrier) gas is in fluidic communication with the adsorbent trap to back-flush the VOCs from the adsorbent trap to an analytical device know as a Gas Chromatograph (GC) for separation and identification.

Conventional purge and trap concentrators typically contain a switching device for the purpose of networking the fluidic communication of purge gas and carrier gas to the adsorbent trap during the desorbtion step. The gas chromatograph typically controls the carrier gas flow rate, as the purge and trap concentrator controls the purge gas flow rate. The pressure and flow rates for the purge and carrier gas usually differ, causing some dead volume issues during the switching of fluidic communication of purge gas pathway to the carrier gas pathway during the desorbtion step. The dead volume can affect the transfer rate and analytical resolution of the extracted VOCs. When sampling an aqueous sample matrix, depending on the carrier gas flow settings and purge and trap desorbtion settings, an unwanted amount of moisture content is sometimes transferred to the gas chromatograph, which affects analytical resolution and detected recovery of the extracted VOCs.

Conventional purge and trap concentrators using a sparge vessel are often used to extract VOCs, typically from an aqueous or a solid sample matrix. The purge and trap concentrators typically consist of three stages for a completed sample analysis cycle: (1) a purge step, (2) a trap desorbtion step, and (3) a bake step. The bake step is a system "cleanup" step used for preparing the system to receive consecutive concentrated samples for analysis. Typically a gas flow is in fluidic communication with the adsorbent trap and the sparge vessel for the purpose of preparing the sample pathway for the next sample analysis. This gas flow typically sweeps the entire sample pathway, while concurrently thermally heating the adsorbent trap to a setpoint temperature higher than the desorbtion setpoint temperature, for the purpose of removing contaminates from the trap in preparation of next sample analysis. If the purge and trap concentrator is connected to a vial auto sampler, such as an EST Analytical Centurion™ Vial Auto Sampler, a heated rinsing liquid (typically deionized water) is flushed through the sparge vessel for cleaning the sparge vessel of unwanted contaminates, concurrent with the bake step. A low amount of carryover of unwanted contaminates sometimes will exist, even in today's purge and trap concentrators.

An improved purge and trap concentrator is needed to detect and prevent foaming without questioning the integrity of the extracted VOCs, to provide a method for removing the remaining contaminates from the sampling pathway that could affect the reporting of analytical data from the subsequent sample analysis, and a method for providing appropriate sampling process parameters to improve overall analytical analysis of extracted VOCs.

SUMMARY OF THE INVENTION

Accordingly, it is an advantage of the present invention to provide an apparatus and method of sampling which delivers a vapor sample to an analyzer instrument using a Desorbtion Mode that has a "split flow" characteristic, which allows a greater volume of gas to be delivered to the analyzer instrument using an arrangement that does not increase the amount of water that is delivered to the analyzer instrument.

It is another advantage of the present invention to provide an apparatus and method of operation that minimizes the amount of time between a bake step at the end of a first sampling cycle and a purge step at the beginning of the next sampling cycle, by using a fan that cools the sparge vessel by thermal convection.

It is yet another advantage of the present invention to provide an apparatus and method of sampling that uses a thermal convection heater for heating a sparge vessel.

It is still another advantage of the present invention to provide an apparatus and method of sampling using a sparge vessel, in which a single sensor is provided that can detect both foaming and an overfill condition.

It is a further advantage of the present invention to provide an apparatus and method of sampling that provides a foam sensor in a sparge vessel, and upon detecting foaming, creates an alternative route for the purge gas that can bypass the frit of the sparge vessel and allow the purge cycle to continue without aborting.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a purge and trap concentrator system is provided, which comprises: a (a) a system controller; (b) a source of gas, which provides a first gas; (c) a plurality of fluidic control devices and a plurality of fluidic passages which fluidically connect the plurality of fluidic control devices; (d) a gas flow control valve that is controlled by a signal from the system controller, the gas flow control valve having a first fluidic inlet and a first fluidic outlet which, under control of the signal, acts to pass a gas flow therethrough, the first fluidic inlet being in fluidic communication with the source of gas and receiving the first gas, the first fluidic outlet dispensing a second gas when required by the signal; and (e) an analytic trap, having: (i) a second fluidic inlet, a third fluidic inlet, and a second fluidic outlet; wherein: (A) the second fluidic inlet is in fluidic communication with the first fluidic outlet of the gas flow control valve, (B) the third fluidic inlet is in fluidic communication with a third outlet of an external instrument, and (C) the second fluidic outlet is in fluidic communication with a fourth inlet of the external instrument; (ii) a first chamber that is coupled to the third fluidic inlet, the first chamber having previously received a concentrated chemical sample, the first chamber acting to remove at least one predetermined substance from the concentrated chemical sample, thereby creating a third "extracted sample" gas flow; and (iii) a second chamber that is coupled to the first chamber, to the second fluidic inlet, and to the second fluidic outlet, the second chamber being configured to receive: (A) the third extracted sample gas from the first chamber, and (B) the second gas from the first fluidic outlet of the gas flow control valve by way of the second fluidic inlet; (f) wherein during a desorbtion procedure: (i) the second gas is received at the second fluidic inlet of the analytic trap, (ii) a fourth gas is received at the third fluidic inlet of the analytic trap from the third outlet of the external instrument; and (iii) at the second chamber the second gas is combined with the third extracted sample gas, thereby creating a larger overall fifth gas flow that now becomes available for analysis by the external instrument.

In accordance with another aspect of the present invention, an analytical chemical sampling apparatus is provided, which comprises: a system controller; a source of inlet gas; a sparge vessel having a purge portion and a sample portion, the purge portion of the sparge vessel receiving inlet gas from the source of inlet gas during a sampling procedure, the sparge vessel being used to house a chemical sample in the sample portion during the sampling procedure, which allows volatile gases to be removed from the chemical sample and directed through at least one fluidic outlet pathway; a source of thermal energy that is proximal to, but spaced-apart from, the sample portion of the sparge vessel; a fan; a temperature sensor located proximal to the sample portion of the sparge vessel, the temperature sensor outputting a first signal to the system controller; a ductwork subassembly that (a) contains the source of thermal energy, (b) receives a first air flow from the fan, (c) directs the first air flow toward the source of thermal energy, thereby creating a second air flow having an increased temperature during a bake procedure, and (d) directs the second air flow toward the sample portion of the sparge vessel during the bake procedure, thereby heating the sample portion of the sparge vessel by use of thermal convection; wherein the system controller is configured to control a bake temperature during the bake procedure, while cleaning the sample portion of the sparge vessel, by using the temperature sensor's first signal to determine a present temperature near the sparge vessel, and by controlling the fan and the source of thermal energy so as to raise the temperature of the second air flow.

In accordance with yet another aspect of the present invention, an analytical chemical sampling apparatus is provided, which comprises: (a) a system controller; (b) a source of gas, which provides a first gas; (c) a gas flow control valve that is controlled by a first signal output by the system controller, the gas flow control valve having a first fluidic inlet and a first fluidic outlet which, under control of the first signal, acts to pass a gas flow therethrough, the first fluidic inlet being in fluidic communication with the source of gas and receiving the first gas, the first fluidic outlet dispensing a second gas when required by the first signal; (d) a plurality of fluidic control devices and a plurality of fluidic passages which fluidically connect the plurality of fluidic control devices, the second gas being directed into the plurality of fluidic control devices and a plurality of fluidic passages; and (e) a sparge vessel having a purge portion and a sample portion, (i) the purge portion of the sparge vessel having a second inlet that, during a sampling procedure, receives the second gas from the gas flow control valve, through the plurality of fluidic control devices and a plurality of fluidic passages; (ii) the sample portion of the sparge vessel being used to house a chemical sample during the sampling procedure, which allows volatile gases to be removed from the chemical sample and directed from the sparge vessel sample portion through a second fluidic outlet; (iii) the sample portion of the sparge vessel including a foam sensor that determines whether the chemical sample undergoes foaming; and (iv) the sample portion of the sparge vessel having a third inlet that, if the chemical sample undergoes foaming to an extent that the foaming is detected by the foam sensor, then under the control of a second signal output by the system controller, the plurality of fluidic control devices and a plurality of fluidic passages change state and re-direct the second gas such that it travels to the third inlet instead of to the second inlet, thereby allowing the sampling procedure to continue during a foaming state while temporarily bypassing the purge portion of the sparge vessel.

In accordance with still another aspect of the present invention, an analytical chemical sampling apparatus is provided, which comprises: (a) a system controller; (b) a source of gas, which provides a first gas; (c) a gas flow control valve that is controlled by a first signal output by the system controller, the gas flow control valve having a first fluidic inlet and a first fluidic outlet which, under control of the first signal, acts to pass a gas flow therethrough, the first fluidic inlet being in fluidic communication with the source of gas and receiving the first gas, the first fluidic outlet dispensing a second gas when required by the first signal; (d) a plurality of fluidic control devices and a plurality of fluidic passages which fluidically connect the plurality of fluidic control devices, the second gas being directed into the plurality of fluidic control devices and a plurality of fluidic passages; (e) a sparge vessel having a purge portion and a sample portion, (i) the purge portion of the sparge vessel having a second inlet that, during a sampling procedure, receives the second gas from the a gas flow control valve, through the plurality of fluidic control devices and a plurality of fluidic passages; and (ii) the sample portion of the sparge vessel being used to house a chemical sample during the sampling procedure, which allows volatile gases to be removed from the chemical sample and directed from the sparge vessel sample portion through a second fluidic outlet; and (f) a sensing subassembly positioned within the sample portion of the sparge vessel at a level above a normal liquid level of the chemical sample, wherein the sensing subassembly comprises: (i) an optical waveguide having a termination end that emits an electromagnetic energy signal at a predetermined wavelength; and (ii) a separate optical sensor that detects the electromagnetic energy signal at the predetermined wavelength, the optical sensor being spaced-apart from the optical waveguide termination end; (g) wherein: (i) if the chemical sample is not exhibiting foaming, and is not exhibiting a high liquid level within the sparge vessel, then the optical sensor receives a substantially steady magnitude of the electromagnetic energy signal at the predetermined wavelength, and the system controller operates normally; (ii) if the chemical sample is exhibiting foaming, then bubbles created by the foaming state tend to interfere with the electromagnetic energy signal, and the optical sensor does not receive a substantially steady magnitude of the electromagnetic energy signal at the predetermined wavelength, and the system controller determines that is should begin operating in an alternative mode; and (iii) if the chemical sample exhibits a high liquid level within the sparge vessel, then the high liquid level tends to interfere with the electromagnetic energy signal, and the optical sensor does not receive a substantially steady magnitude of the electromagnetic energy signal at the predetermined wavelength, and the system controller determines that is should begin operating in the alternative mode; and (iv) the system controller thereby is able to detect both a foaming condition and a high liquid level state using a single optical sensor.

In accordance with a further aspect of the present invention, a method for operating a purge and trap concentrator system is provided, in which the method comprises the following steps: (a) providing a system controller, a gas source that supplies a first gas flow, a plurality of fluidic control devices and a plurality of fluidic passages which fluidically connect the plurality of fluidic control devices, an analytic trap, a first fluidic inlet that is in communication with an external analyzer instrument, and a first fluidic outlet that is in communication with the external analyzer instrument; (b) receiving a second gas flow from the external analyzer instrument, through the first fluidic inlet; (c) placing a concentrated chemical sample into a first chamber of the analytic trap, directing the second gas flow into a first end of the first chamber and removing at least one predetermined substance from the concentrated chemical sample, thereby creating an "extracted sample" gas flow that is directed to a second end of the first chamber; and (d) receiving, at a second chamber of the analytic trap, the extracted sample gas flow from the first chamber; receiving, at a second inlet of the second chamber of the analytic trap, the first gas flow from the gas source; and combining the first gas flow and the extracted sample gas flow at the second chamber and to create an enhanced gas flow that is directed through a second outlet of the second chamber and further to the first fluidic outlet, and to the external analyzer instrument, thereby providing a larger overall enhanced gas flow that now becomes available for analysis by the external analyzer instrument.

In accordance with a yet further aspect of the present invention, a method for operating an analytical chemical sampling apparatus is provided, in which the method comprises the following steps: (a) providing a system controller, a gas source that supplies a first gas flow, a plurality of fluidic control devices and a plurality of fluidic passages which fluidically connect the plurality of fluidic control devices, a sparge vessel having a purge portion and a sample portion; (b) placing a chemical sample into the sample portion of the sparge vessel, and during a sampling procedure, receiving the first gas flow at a first inlet at the purge portion of the sparge vessel, thereby removing volatile gases from the chemical sample and directing the volatile gases past a foam sensor and to a first fluidic outlet where the volatile gases leave the sparge vessel; and (c) if the chemical sample undergoes foaming to an extent that the foaming is detected by the foam sensor, then, under the control of the system controller, changing a state of the plurality of fluidic control devices and a plurality of fluidic passages to re-direct the first gas flow such that it instead travels to a second inlet at the sample portion of the sparge vessel, thereby allowing the sampling procedure to continue during a foaming state while temporarily bypassing the purge portion of the sparge vessel.

In accordance with a yet further aspect of the present invention, a purge and trap concentrator system is provided, which comprises: (a) a system controller; (b) a first source of gas, which provides a first gas; (c) a plurality of fluidic control devices and a plurality of fluidic passages which fluidically connect the plurality of fluidic control devices; (d) a variable flow rate gas flow control valve that is controlled by a first signal from the system controller, the gas flow control valve having a first fluidic inlet and a first fluidic outlet which, under control of the first signal, acts to pass a gas flow therethrough, the first fluidic inlet being in fluidic communication with the source of gas and receiving the first gas, the first fluidic outlet dispensing a second gas when required by the first signal; (e) an external instrument, which includes second source of gas that supplies a third gas, the external instrument having a second fluidic outlet that supplies the third gas, and a second fluidic inlet; and (f) an analytic trap, having: (i) a first trap port, a second trap port, and a third trap port; wherein: (A) the first trap port is selectively in fluidic communication with the first fluidic outlet of the gas flow control valve, (B) the second trap port is selectively in fluidic communication with a vent, through the plurality of fluidic control devices and plurality of fluidic passages, and is selectively in fluidic communication with the second fluidic output of the external instrument, through the plurality of fluidic control devices and plurality of fluidic passages, and (C) the third trap port is selectively in fluidic communication with the second inlet of the external instrument; (ii) a first chamber that is coupled to the second trap port, the first chamber being designed to receive a concentrated chemical sample, the first chamber acting to remove at least one predetermined substance from the concentrated chemical sample, and thereby create an "extracted sample gas flow"; (iii) a second chamber that is coupled to the first chamber, to the first trap port, and to the third trap port; and (iv) a trap heater; (g) wherein, before a desorbtion procedure begins: (i) the plurality of fluidic control devices are in a first state; (ii) the second gas is received at the first trap port of the analytic trap, and flows into the first chamber; (ii) a fourth gas exits the first chamber at the second trap port, and flows toward a vent, through the plurality of fluidic control devices and plurality of fluidic passages, including a vent valve that is open at this time; (iii) then the vent valve is closed by a second signal from the system controller, and the fourth gas begins to build a desorbtion pressure control ("DPC") pressure at the second trap port, wherein the DPC pressure is controlled by the gas flow control valve, which is controlled by the first signal from the system controller; and (iv) the DPC pressure reaches a predetermined magnitude; and (h) wherein, a desorbtion procedure begins, such that: (i) the plurality of fluidic control devices are activated into a second state, under the control of a third signal from the system controller; (ii) the third gas from the second outlet of the external instrument now flows to the second trap port and into the first chamber; (iii) the extracted sample gas flow travels from the first chamber into the second chamber; and (iv) a fifth gas flow, which includes the extracted sample gas flow, exits the second chamber at the third trap port and flows toward the second inlet of the external instrument, through the plurality of fluidic control devices and plurality of fluidic passages.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The above-mentioned and other features and advantages of this invention, and the manner of attaining them, will become more apparent and the invention will be better understood by reference to the following description of at least one embodiment of the invention taken in conjunction with the accompanying drawings. The accompanying drawings incorporated in and forming a part of the specification illustrate several aspects of the present invention, and together with the description and claims serve to explain the principles of the invention. In the drawings:

DETAILED DESCRIPTION OF THE INVENTION

Reference will now be made in detail to the present preferred embodiment of the invention, an example of which is illustrated in the accompanying drawings, wherein like numerals indicate the same elements throughout the views. The exemplification(s) set out herein illustrate(s) at least one preferred embodiment of the invention, in at least one form, and such exemplification(s) (is)(are) not to be construed as limiting the scope of the invention in any manner.

The terms "first" and "second" preceding an element name, e.g., first inlet, second inlet, etc., are used for identification purposes to distinguish between similar or related elements, results or concepts, and are not intended to necessarily imply order, nor are the terms "first" and "second" intended to preclude the inclusion of additional similar or related elements, results or concepts, unless otherwise indicated.

Figure 1A:
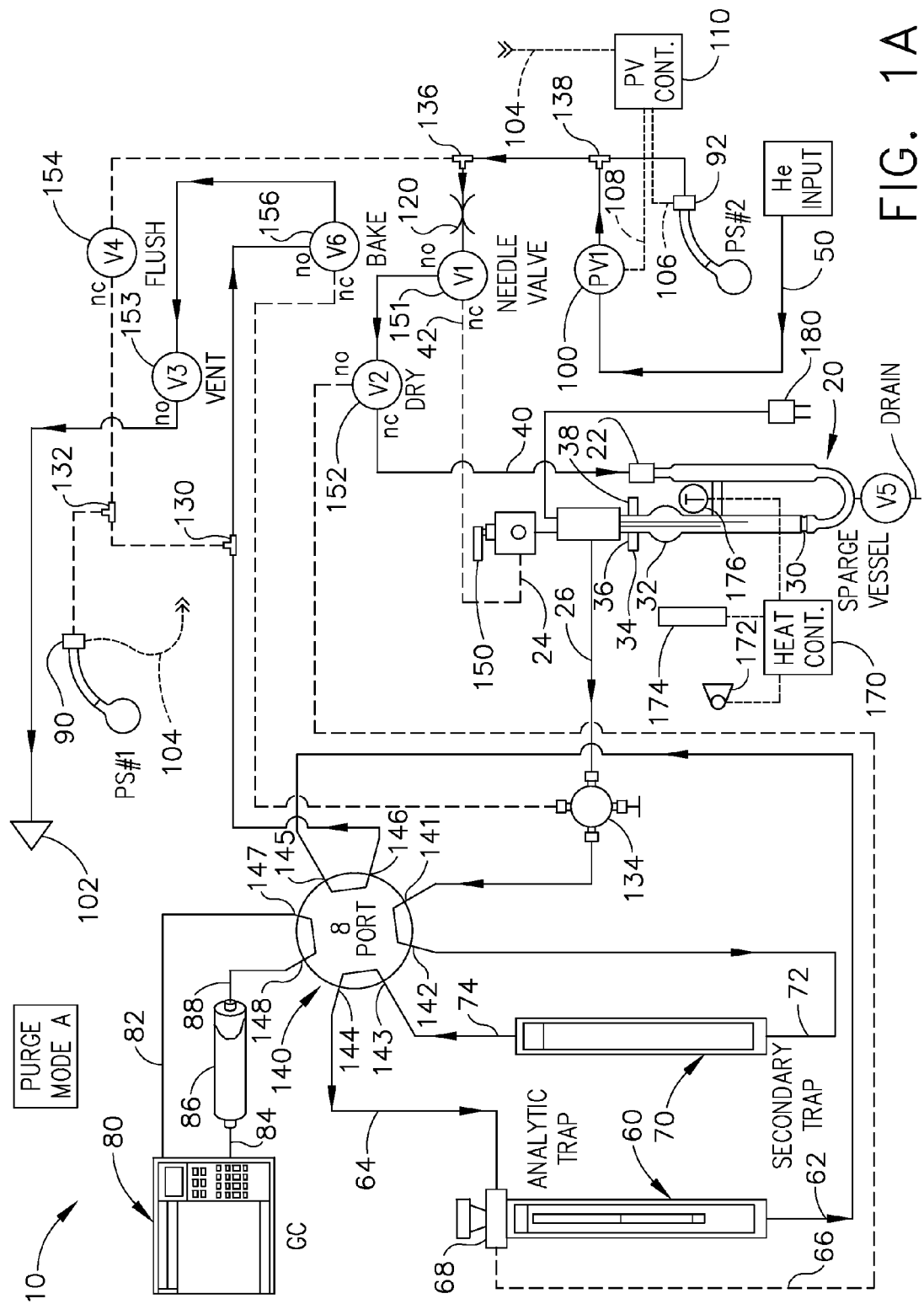
FIG. 1A is a fluidic schematic diagram of a purge and trap concentrator system constructed according to the principles of the present invention, showing the system in an operating mode called "Purge Mode A."

Referring now to FIG. 1A, a fluidic schematic diagram is provided, generally designated by the reference numeral 10, for a first purge mode, in which a VOC (volatile organic compound) sample is extracted from an aqueous sample contained in a sparge vessel 20. Several different fluidic diagrams are provided herewith, and they all generally contain the same hardware, but are configured in different arrangements. This description will start by introducing the hardware.

The fluidic diagram 10 includes five different solenoid valves, which are either two-way or three-way valves, designated 151, 152, 153, 154, 155, and 156 (or V1, V2, V3, V4, V5, and V6). There is also an eight-port (four-way) valve 140, in which some of its passageways can be repositioned by rotating or otherwise actuating the valve 140. There is a proportional flow control valve 100 (also referred as PV1) that generally receives helium gas from an input source of helium gas at 50, and there is a vent to atmosphere at 102. There is a fluidic inlet at 82 that receives carrier gas from an analyzer instrument 80, in general which will be referred to as a gas chromatograph (or "GC") for this description of the present invention. There is also a fluidic outlet 84 that sends gas samples to the same GC analysis instrument 80.

The various solenoid valves in the system 10 are also referred to by names, as follows: V1 at 151 is referred to as the "Needle Valve;" V2 at 152 is referred to as the "Dry Purge Valve;" V3 at 153 is referred to as the "Vent Valve;" V4 at 154 is referred to as the "Backflush" or simply "Flush" valve; V5 at 155 is referred to as the "Drain Valve;" and V6 at 156 is referred to as the "Bake Valve." These valves will be energized or de-energized as required by the system controller, for the various modes of operation of the system 10. Drain Valve V5 is used to drain the sparge vessel 20, at appropriate times during the processing cycles of the purge and trap analytical instrument 10. The valves in system 10 are sometimes referred to herein as a "plurality of fluidic control devices;" the passageways between the valves are sometimes referred to herein as a "plurality of fluidic passages."

It will be understood that the valves V1-V6 and the four-way valve 140 can comprise virtually any type of automatically-controlled valves, including solenoids that are actuated by electrical signals. Various control valves are also available that can be actuated by hydraulic or pneumatic signals, for example, which could be used in the present invention, in combination with, or in lieu of, the electrically-controlled solenoids described herein and in the drawings. Moreover, the control techniques could use either "analog" or "digital" control signals, and the automatically-controlled valves could then be either "on-off" digital control valves, or proportional analog control valves, for example. Of course, in the illustrated embodiment, digitally-actuated solenoid valves are used. The various automatically-controlled valves used in the present invention generally are used to allow vapors or liquids to pass therethrough (or to block them from doing so), and thus are generally referred to as "fluidic valves."

The proportional flow control valve 100 (PV1) is also referred to herein as a "gas flow control valve" and also as a "pressure control valve." Valve 100 has a fluidic inlet that receives source gas from the gas input passageway 50, and valve 100 has a fluidic outlet that sometimes has an "output gas" passing therethrough. Whether or not gas passed through the fluidic outlet depends on the control signal (at 108) received by the valve 100. Since valve 100 is a variable operating device, the gas flow at its outlet can be 100% of the gas flow at its inlet, thereby allowing a maximum pressure to be achieved downstream from valve 100. On the other hand, valve 100 can be controlled to allow only a fraction (or zero) of the inlet gas to pass therethrough to its outlet. Valve 100 typically operates as a pressure control valve, and most of its operations (as discussed below) will be based on controlling its outlet pressure, and its system controller 110 (discussed below) typically controls from a programmable pressure setpoint that acts as the process control variable. The setpoint value changes, depending on which operating mode is currently being used.

The fluidic diagram 10 includes a sparge vessel 20 that has two major portions or "sides" which create a generally U-shaped appearance. The sparge vessel can be filled with a liquid, such as distilled or deionized water or other liquid of interest, and receives neutral gases on the "input" side, and has a heater that will tend to heat up (and later cool off) the "output" or "sample" side. This "sample portion" is generally indicated at the reference numeral 28 (see FIG. 11), which is where the sample to be analyzed is placed. A first inlet on the input side of the sparge vessel is indicated at reference numeral 22, while a second inlet at 24 is located near the outlet (or output) side of the sparge vessel. There is also a shut-off valve at 150 near this second inlet 24. The outlet passageway for the sparge vessel is at reference numeral 26.

The sparge vessel 20 receives some type of pressurized gas along either a pipe or tube 42 or 40, and these pipes/tubes are connected to either a Needle Valve 151 (V1) or a Dry Purge Valve 152 (V2). In general, the flow of gases starts at a helium input source through its inlet tubing or piping at 50, through the proportional flow valve 100 (PV1), through a T connection 138, through a second T connection 136, through a flow restrictor 120, through the Needle Valve 151, and finally through the Dry Purge Valve 152. This gas arrives at the inlet of the sparge vessel at 22, and then passes into the "sample portion" 28 of the sparge vessel 20.

Within the sparge vessel itself is a frit 30 that disperses the gas into many fine streams to increase surface contact of the gas with the sample for extraction of volatile gases (e.g., VOCs). An enlarged portion (the "foam bubble" portion) of the sparge vessel glassware is at 32, where samples have a tendency to foam. Sparge vessel 20 has a sensing subassembly at 34 which comprises a fiber optic cable 36 and an optical sensor 38. The optical sensor 38 is on the opposite side of the sparge vessel glassware from the fiber optic cable 36 that emits a light source (i.e., it is spaced-apart from the fiber optic cable 36). This will be discussed below in greater detail. The outlet of the sparge vessel at 26 is in fluidic communication with a four-way X connection 134, and further with the eight-port valve 140 and/or the Bake Valve 156 (V6).

There are two pressure sensors 90 and 92 in the system, also referred to as "PS#1" and "PS#2," and there is a temperature sensor 176 in the sparge vessel area. There are some "tees" that act as three-way passages, at 130, 132, 136, and 138, and there is an "X" connection that acts as a four-way passage at 134. Pressure sensor 90 (PS#1) is used for regulating the back pressure in the fluidic system 10. The pressure sensor 92 (PS#2) is used to maintain the appropriate flow rate through the fluidic system 10, as controlled by the proportional valve 100. As will be understood from the fluidic schematic diagrams presented herein, pressure sensor 92 is positioned at or near the output side of the proportional valve 100.

If the temperature sensor 176 is a thermocouple, as in an exemplary embodiment, then a K-type thermocouple plug and cable can be used, as designated at reference numeral 180. This will allow the sparge vessel subassembly 20 to be dismounted (and re-mounted) in the overall system 10 while allowing the thermocouple to be easily disconnected and (re-connected).

On the input side of the sparge vessel is a restrictor 120 that narrows the inner diameter of the tubing between the tee 136 and the Needle Valve V1. The restrictor 120 also can be of many forms, but in the illustrated embodiment it comprises a length of tubing or piping that exhibits a predetermined volume, for example a tube about 70 inches in length with an inner diameter of about 0.015 inches.

There are two different traps 60 and 70 in the system depicted in the flow diagram 10. The trap 60 is an "analytic trap" which can act as a condensate trap or an adsorbent trap, while the trap 70 is generally used as a secondary adsorbent trap.

The analytic trap 60 has inlets and outlets at three places: at 62, it is connected to the eight-port valve at its port 145; at 66, it is connected to the Dry Purge Valve 152; and at 64, it is also connected to the eight-port valve at its port 144. The secondary trap 70 is connected at 72 to the eight-port valve at its port 142, and at 74 it is connected to the eight-port valve at its port 143. The analytic trap 60 has a "top portion" at 68 that can be used to receive additional carrier gas in a particular mode of operation, as discussed below in greater detail.

The eight-port valve 140 has eight different inlet and outlet ports, and the definitions (or uses) of these ports can be altered, depending upon the direction or destination of gas flow through those ports. These various ports are designated 141-148. The port 147 is connected to the GC output at 82, while the port 148 is ultimately connected to the GC input at 84. There is a heater 86 in the transfer line between the outlet passageway 88 from the eight-port valve 140 and the inlet passageway 84 to the GC instrument 80. This allows the gaseous samples being sent to the GC to remain at an elevated temperature for analytical purposes.

Various other passageways in the system 10 are indicated on FIG. 1A. FIG. 1 also depicts two controllers, including a heater controller 170 and a proportional valve controller 110. The proportional valve controller 110 receives a pressure signal from the pressure sensor 90, in which the pressure signal at 104 travels to the proportional valve controller 110. The controller 110 outputs a signal along the pathway 108 to the proportional valve itself at 100. The valve controller 110 also receives a second pressure sensor signal from the sensor 92 along a pathway 106. These pressure signals are used for the proper control of the proportional valve 100 for the various modes of operation that will be described below in the flow charts.

The heater controller 170 receives a temperature signal from a temperature sensor 176 that is placed within the sparge vessel on its sample portion at 28. This arrangement is better viewed on FIG. 11. The heater controller 170 has output signals that control a fan (or blower) 172 and a set of resistance heating elements at 174. In one form of the present invention, the resistance heating elements 174 are constructed as multiple coils of resistive wire, which act as a source of thermal energy.

In general, the heater controller 170 will be used to raise the temperature of the sparge vessel sample portion 28 when it is time to extract VOCs from the sample. When this occurs, the heater controller 170 will generally use proportional-integral-differential (P-I-D) control operating principles to increase or decrease the speed of the fan. Moreover, P-I-D-type control principles will generally also be used to control the amount of current flowing through the resistive heating elements 174.

Both the fan speed and the percentage of duty cycle of current sent to the resistive heating elements 174 can be independently controlled, so that full heat, or zero (0) heat, or any percentage in between (within the resolution of the controller) can be obtained at any particular instant of time. In addition, at the end of the sample extraction process, and after the end of a bake cycle, the blower 172 can be run at "full speed" with the heating elements 174 turned OFF, thereby quickly cooling the sample portion 28 of the sparge vessel 20. By use of convection heating and cooling, the present invention allows for not only precise control for heating the sparge vessel, but also for very quick cooling, which is something that has not been achieved in prior systems that simply use either radiation or conductive thermal transfer (for increasing the sparge vessel temperature, not to decrease it).

In an alternative mode of the present invention, the output percentage of the fan speed and the output percentage of the current for the resistive heating elements 174 can be controlled in a manner in which the numeric value of one of these outputs is related to the numeric value of the other output (instead of each being independent of the other). For example, if the fan speed output in percent is called "F" and the heating element current output in percent is called "I", then these two output values could be related in an "additive inverse" relationship, such that F+I=100%. In this example, if the fan speed (F) is at 10%, then the current (I) would be at 90%; or if F is 20% then I is 80%, and so on. In this manner, the heating system controller 170 will be able to vary the overall thermal energy transfer to the sparge vessel by controlling either F (or I) using a P-I-D algorithm, and the opposite variable I (or F) will automatically have its value calculated using a linear equation (such as F+I=100%). In this example, the higher the current (I), the greater the heat transfer to the sparge vessel; the higher the fan speed (F), the greater the cooling of the sparge vessel (both because the current would be less, and also the faster the air flow, the greater the cooling effect will likely be). Of course, if F is 0% and I is 100%, then there would be virtually no convective air flow to the sparge vessel, so this would not truly provide the maximum heating effect (although the blower motor might not be able to actually stop rotating instantaneously). On the other hand, if F is 100% and I is 0%, then this would provide the maximum cooling effect.

In another alternative mode of the present invention, the "additive inverse" relationship could include an "offset" value, such that F+I does not equal 100%, but instead it will equal 110%, or 120%, or perhaps even 200%. For example, if F+I=200%, then the fan and current would always be "pegged" at 100% output each, for maximum heating capability. This, of course, would not allow the P-I-D controller 170 to operate in its usual fashion, so a more realistic approach would be F+I=120%, or F+I=130%. In the example where F+I=120%, if F is 50%, then I is 70%; and if F is 20%, then I is 100%. The offset value could even be a negative number, such that F+I=80% or 90%, for example, although this probably would be "wasting" some heating system capacity.

The P-I-D controller 170 could typically calculate the desired current (for example) several times per second, and then vary the signal value for I accordingly. Then a very small portion of the controller's processing power would easily be able to calculate the appropriate value for F. In this manner the output values for both F and I will be modified several times per second, using a single P-I-D control algorithm. However, if it is desired to not quickly and repeatedly modify the fan motor speed many times over a typical bake cycle (e.g., for mechanical reasons), then the P-I-D controller can be used to directly control the fan speed (F) at a less frequent rate, and the value for I will be automatically modified at the same (less frequent) rate.

It will be understood that any realistic offset value could be used for the F+I equation, and still be within the principles of the present invention. A small positive offset value will likely be preferred (so that F+I is equal to 110% or 120%), but this really depends upon (a) how much heating capacity is provided by the resistive heating elements 174 and (b) how much air flow capacity is provided by the fan (or blower) 172, for a given sparge vessel system design. It will also be understood that the variables F and I can be related by a different type of equation; or that each can be independently controlled by its own P-I-D algorithm (as noted above). Moreover, during the cooling mode after a bake cycle, any control equation in which F+I is equal to a number greater than 100% would be suspended; in other words, to achieve maximum cooling, the current I should be held at 0%, regardless of the fan speed (which would typically be run at 100% during cooling mode).

In FIG. 1A, the eight-port valve is in "Position A," the Needle Valve 151 (V1) is turned OFF, while the Dry Purge Valve 152 (V2) is turned ON. This allows the Purge Mode A to occur, in which helium gas is sent through the proportional valve 100, Needle Valve 151, Dry Purge Valve 152, and into the sparge vessel inlet at 22. The VOCs that are extracted leave the sparge vessel at its outlet 26 and travel to the eight-port valve at its port 141. These gases continue to the secondary trap 70, through the eight-port valve at ports 143 and 144, and then to the analytic trap 60. The gases that escape the traps continue through the passageway 62 back to the eight-port valve at its ports 145 and 146, through the de-energized Bake Valve 156 and through the de-energized Vent Valve 153, where these gases are vented at the vent 102. At this time, the gas chromatograph 80 can be controlled to inject gases at 82 through the eight-port valve ports 147 and 148, and then back to the GC at 84. This GC gas flow may not be required, but is available in the Purge Mode A, if desired.

As noted above, if the sample that is being purged begins to foam, and if the foaming is unattended, the sample could come into contact with internal pathway components and thereby contaminate the entire system. The sample is typically either an aqueous or a solid sample matrix, and is housed in the sealed sparge vessel (in the sample portion). The inlet or "purge" gas is swept through the concentrated chemical sample at a controlled flow rate, to extract the VOCs from that sample.

Figure 1B:
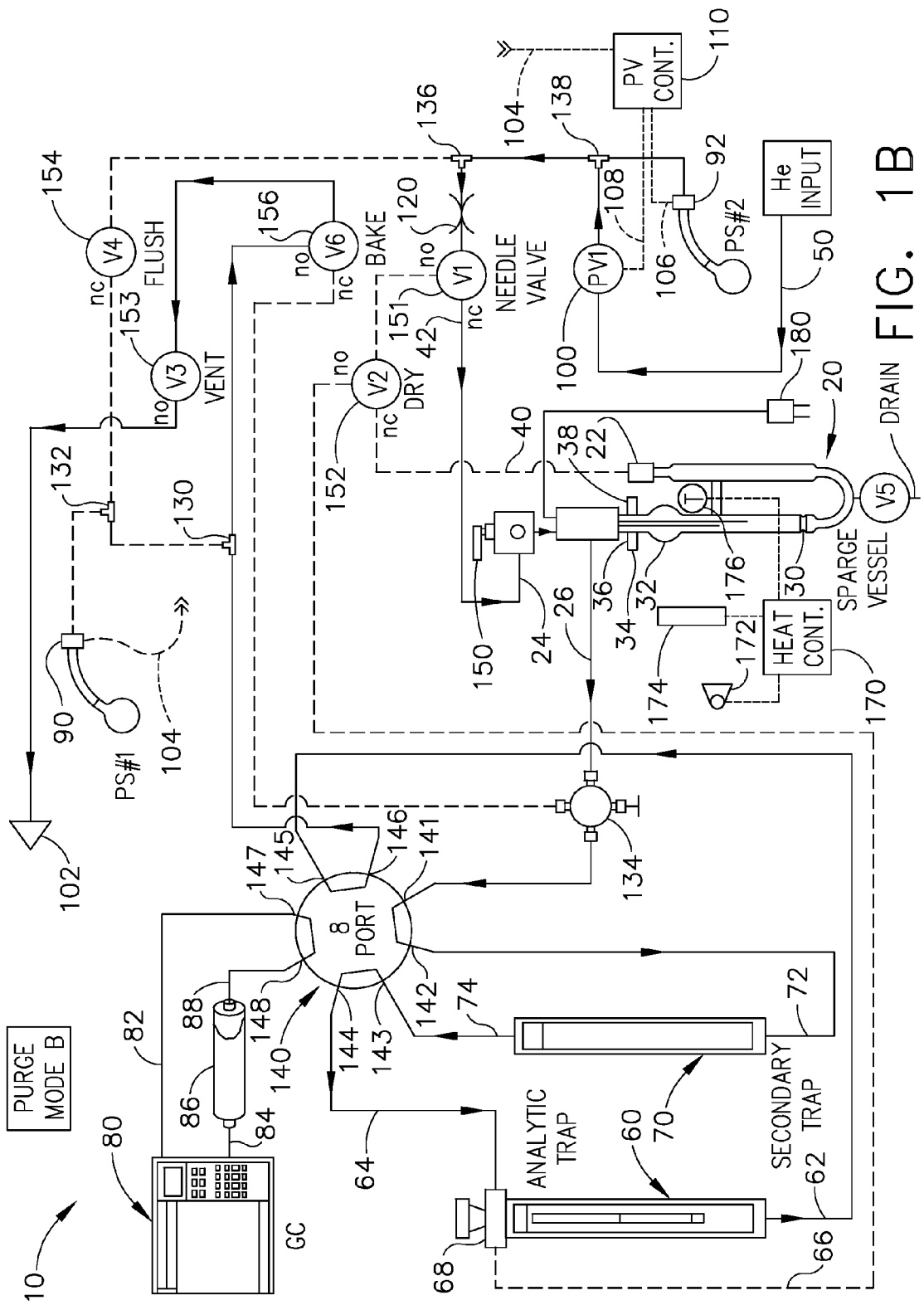
FIG. 1B is a fluidic schematic diagram of the purge and trap concentrator system of FIG. 1A, showing the system in an operating mode called "Purge Mode B."

By use of the sensing subassembly 34 as a foam sensor, the system 10 can detect if foaming begins to occur. The sparge vessel contains the enlarged area, also referred to as a "foam bubble" 32, which will tend to catch the foam and break it up before exiting the sparge vessel. Foam sensor 34 is placed above (e.g., higher in elevation than) the foam bubble 32, and if the foam reaches that point, then the system is about to encounter a problem. FIG. 1B shows an alternative Purge Mode (referred to as "Purge Mode B") that shows how the present invention can address the foaming problem.

If the chemical sample is not exhibiting foaming, then the flow path of the helium gases does not change. However, if the chemical sample exhibits foaming to an extent that the foam sensor is triggered, it will electrically control the Needle Valve 151 and cause it to turn on. This changes the flow path of the helium gases so that they travel through the passageways 42 and 24 to the top portion of the other side of the sparge vessel. This effectively re-routes (or "re-directs") the purged gas to the second inlet at 24 to allow the sampling procedure to continue without aborting the sampling procedure itself. Except for this re-routing, the rest of the flow diagram of FIG. 1B is the same as that of FIG. 1A.

The VOCs of interest remain in the analytic traps 60 and 70, and after the extraction process has been completed (during a desorbtion step), those retained VOCs will be removed from the analytic absorbent trap and transferred to the GC 80. This occurs during other modes of operation, to be discussed below, and involves switching the eight-port valve to its "Position B." In Purge Mode B, the eight-port valve 140 remains in its Position A, the Needle Valve 151 is turned ON, the Dry Flush Valve remains ON, and the Vent Valve 153 remains ON.

Figure 2:
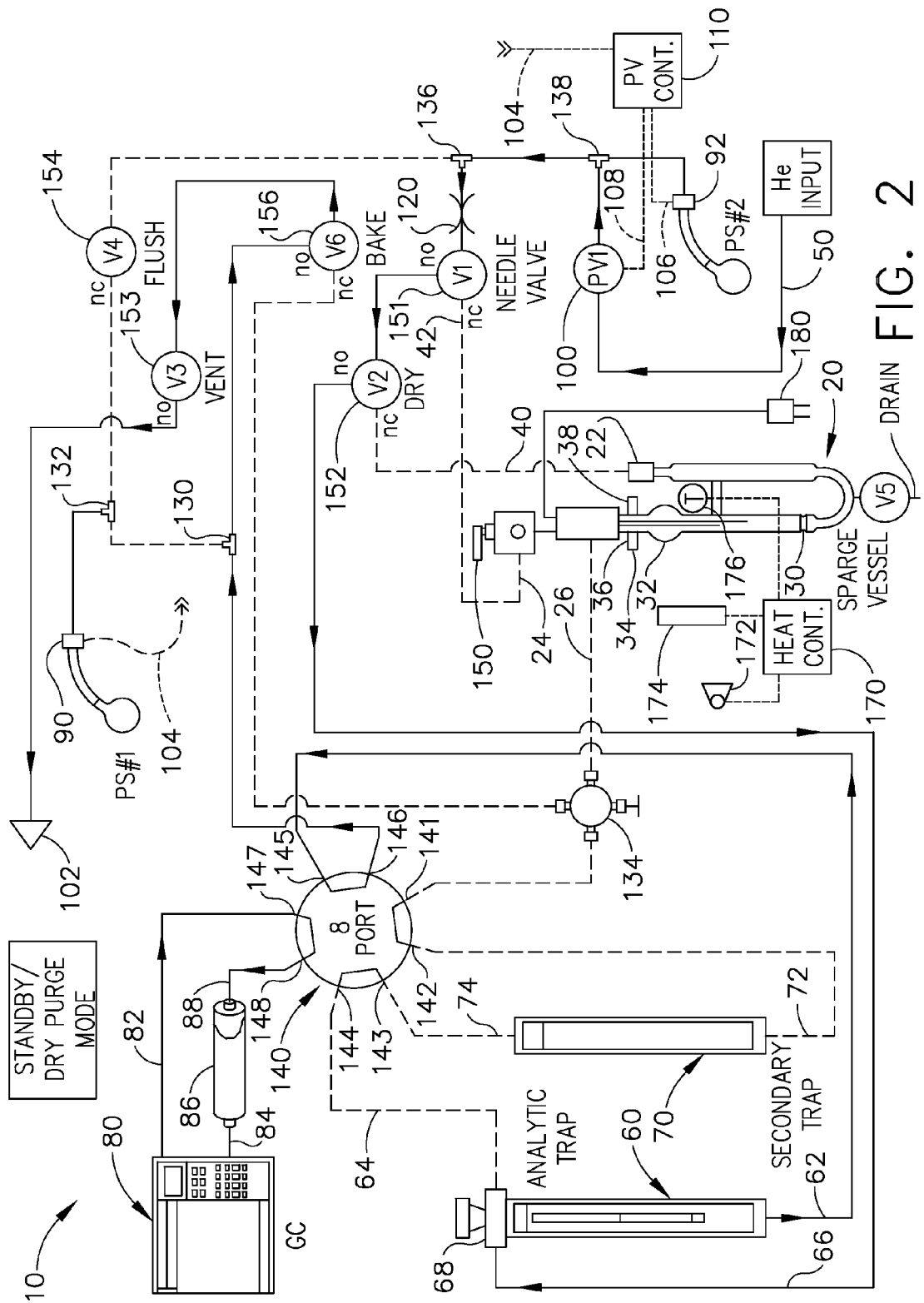
FIG. 2 is a fluidic schematic diagram of the purge and trap concentrator system of FIG. 1A, showing the system in an operating mode called "Standby—Dry Purge Mode."

Referring now to FIG. 2, the system 10 is configured for either the Standby Mode or the Dry Purge Mode of operation. The Standby mode is the first mode encountered when initially turning on the purge and trap analyzer instrument 10. This is the step 200, at the beginning of the flow chart on FIG. 6. This Standby mode happens to have the same type of fluidic flow movement as in the "Dry Purge" mode, which is encountered at step 280 on FIG. 8.

During the Dry Purge mode (or Standby mode) the gas pressure source (such as helium or nitrogen) flows gas through the proportional valve 100 (PV1) according to a "Dry Purge Flow" setpoint control program. The gas flow then is directed to the needle valve 151, which is turned OFF so the flow is then directed to the Dry Purge valve 152. This valve is also turned OFF, and the gas flow is directed along passageway 66 to the top of the analytic trap at 68. The gas flows through the trap 60, and then out the passageway 62 to the eight-port valve at its port 145, leaving its port 146 so the gas flow then travels to the Bake Valve 156. The gas continues to travel to the Vent Valve 153, which is de-energized and the gas flows out its normally open port and to the vent 102. This would typically be a relatively low pressure gas flow, and the Dry Purge pressure setpoint can be set by the user, but will have a default pressure setpoint value in the control program.

The gas flow control valve 100 (PV1) is adjustable (as determined by the pressure controller 110), and it controls the gas pressure in the trap 60 prior to the desorbtion step.

The gas flow from the GC instrument 80 is also allowed to flow through its outlet 82, and then through the ports 147 and 148 of the eight-port valve 140. This gas flow then travels through the passageway 88, heater 86, and the inlet passageway 84 of the GC instrument 80. Again, this can be a relatively low pressure flow, as desired by the user. Since this is also the configuration of the Standby Mode, the flow rates discussed above can be either higher or lower depending upon the pressures used and controlled by the proportional valve 100, or at the outlet of the GC instrument 80, depending upon the user's setpoint pressure preferences for the Standby mode versus the Dry Purge mode.

Figure 3:
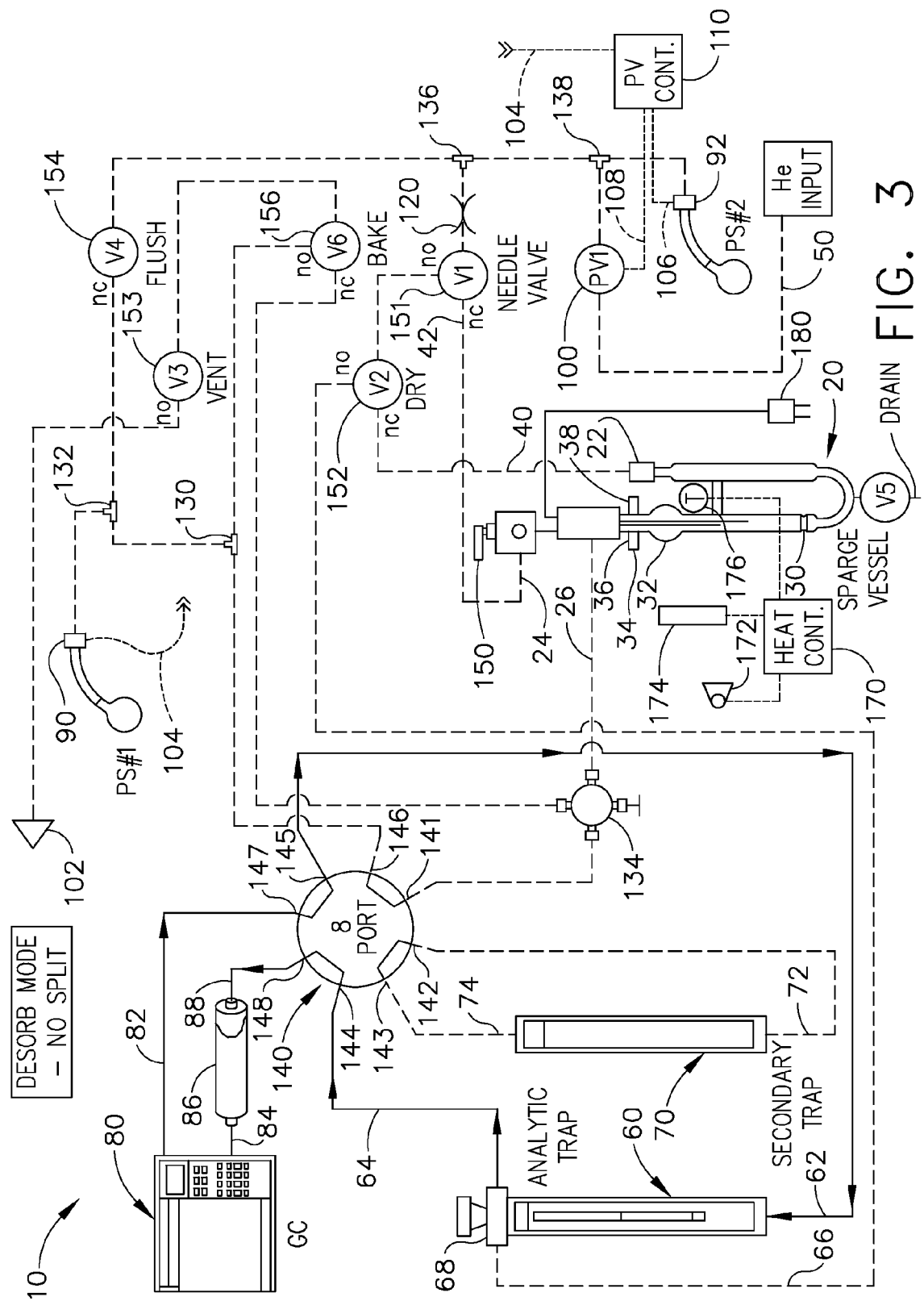
FIG. 3 is a fluidic schematic diagram of the purge and trap concentrator system of FIG. 1A, showing the system in an operating mode called "Desorb Mode—No Split."

Referring now to FIG. 3, the system 10 is illustrated in a "Desorb" Mode of operation, which is short for "Desorbtion." In FIG. 3, the mode of operation is also referred to as a "No Split" Mode, which will be described in greater detail below. In the Desorb Mode, the eight-port valve is switched to its Position B, so that the compounds of interest that have been trapped in the analytic trap 60 can be sent to the GC 80. In this mode, the injection gas from the GC at its outlet 82 flows through the eight-port valve at its ports 147 and 145, and continues to the "bottom" of the trap 60 at the passageway 62. The compound or compounds of interest are removed from the trap while it is being heated to a predetermined temperature during this gas flow of the Desorbtion Mode. These compounds are directed through a passageway 64 and to the eight-port valve through ports 144 and 148, and to the outlet 88. After passing through the heater 86, the compounds of interest are directed to the inlet of the GC at 84. This is a fairly standard mode of operation for analyzer instruments of the type sold by various companies, including EST Analytic, the assignee of the present invention.

In FIG. 3, the method parameter is desorbtion pressure control. The pressure sensor 90 sends a signal along 104 to the proportional valve controller 110. At a predetermined pressure, the system vent 102 can be closed by use of the Vent Valve 153. This action will seal off the fluidic pathway at the predetermined setpoint value prior to the desorbtion step, if desired. This is an alternative desorbtion mode, which is illustrated on FIG. 4.

Figure 4:
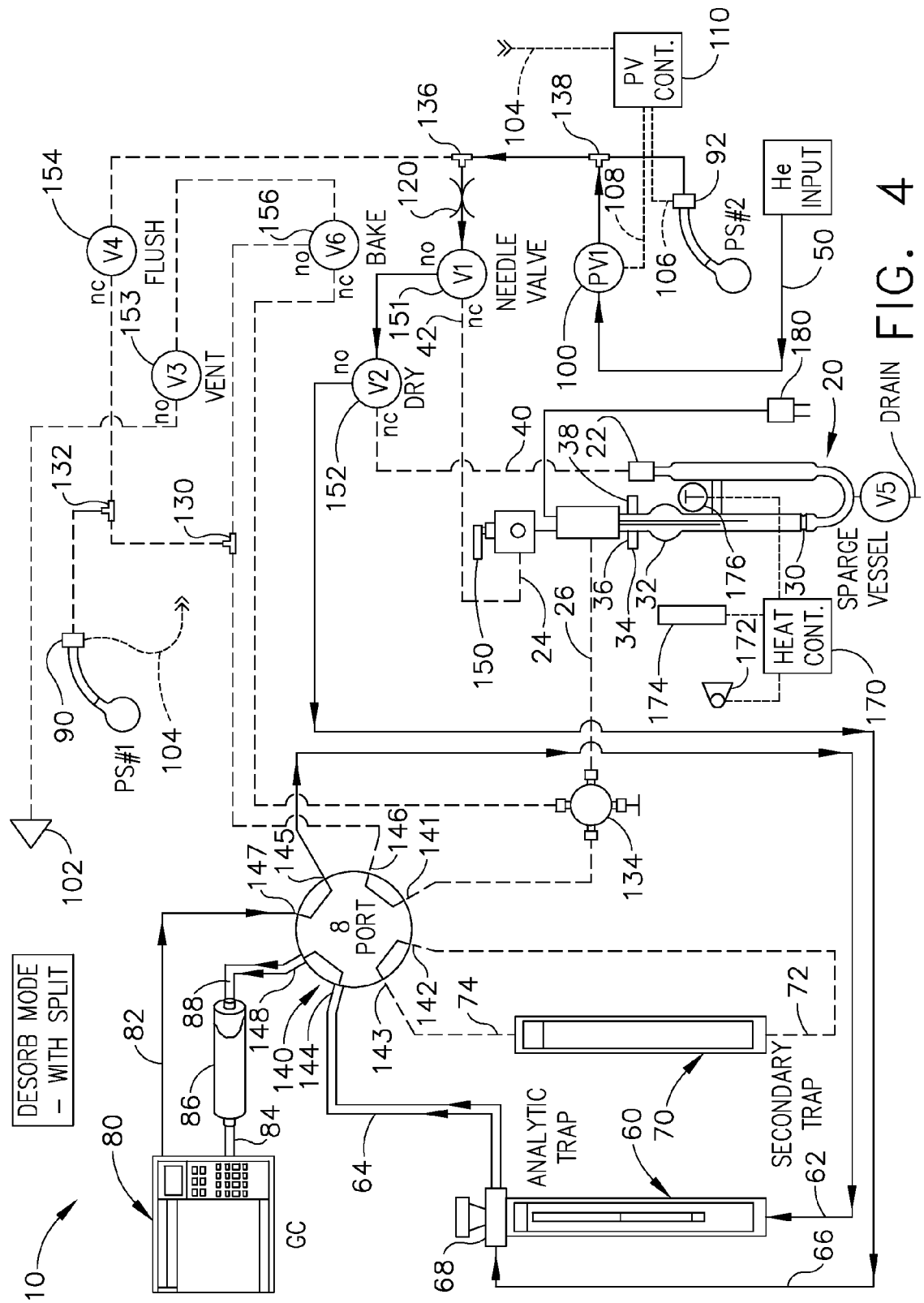
FIG. 4 is a fluidic schematic diagram of the purge and trap concentrator system of FIG. 1A, showing the system in an operating mode called "Desorb Mode—With Split."

In FIG. 4, the alternative desorbtion mode is referred to as the Desorb Mode "With Split." The proportional valve controller 110 receives a signal at 106 from the other pressure sensor 92. This signal is used to control the proportional valve 100 for controlling the desorbtion gas flow rate that is in fluidic communication with the analytic trap 60, which is also in communication with the GC 80. A feedback loop is thus created by using the pressure signal from the sensor 92 to control the proportional valve 100, for controlling the gas flow rate which will eventually reach the analytic trap 60 and the GC 80.

In FIG. 4, the gas flow travels from the proportional valve 100 through the Needle Valve 151, Dry Purge Valve 152, and into a passageway 66 that reaches the analytic trap 60 at its "top portion" 68. This effectively adds an additional gas stream to the desorbtion pathway, and is referred to in the present invention as the "Split Flow" arrangement. In essence, the trap 60 has a "first chamber" that is coupled to a fluidic inlet that receives the gases from the GC 80, through the passageway 62. This "first chamber" had previously received a concentrated chemical sample from the sparge vessel 20 during a previous step of the analysis procedure. As the gases from the GC pass through the first chamber, it acts to remove at least one predetermined substance of interest from said concentrated chemical sample, and thus an "extracted sample" gas flow is created that passes from the first chamber.

Trap 60 also contains a "second chamber" in essence, which is the top portion 68. The second chamber is coupled to the first chamber, such that the extracted sample gas flow passes from the first chamber into the second chamber. This second chamber 68 is also coupled to a fluidic inlet that is in fluidic communication with the passageway 66, and thus back to the PV1 valve 100, and finally back to the input gas source via the passageway 50. Therefore, the second chamber receives both the extracted sample gas flow from the first chamber and the inlet gases from the PV1 valve 100.

In this manner, the additional gas flow through the top portion 68 of the analytic trap 60 combines with the GC's own helium gas flow, which the GC provided through the outlet 82 through the eight-port valve 140 and into the bottom of the trap at 62. Thus, both of these gas flows travel through the pathways 62 and 66, and thereby exit the analytic trap through the passageway 64, back through the eight-port valve 140 and back to the GC at its inlet 84. This is a way of obtaining a greater volume of gas samples for the GC, and occurs without drawing water from the analytic trap 60, due to the gas flow through the passageway 66. The greater gas volume allows the GC to achieve a greater sensitivity when measuring for the chemical composition of interest in the sample gases received at its inlet 84.

This operating mode is also referred to as the "Desorb Column Pressure" Mode. The pressure control valve 100 (PV1) can maintain or increase the pressure in the trap 60 so that it operates at a predetermined split flow pressure setpoint. Once the system pressure at pressure sensor 92 reaches a predetermined setpoint, the proportional valve 100 (PV1) can be turned OFF (to its 0% output), and this will stop the flow through the passageway 66 entering the analytic trap 60. Once that occurs, the "Split Flow" Mode will no longer continue.

It will be understood that the flow control valve 100 (PV1) does not necessarily need to have a proportional flow capability to perform in this "Split Flow" mode of operation. In other words, as an alternative embodiment, the control valve 100 could be replaced by a standard "ON-OFF" gas valve (e.g., a solenoid valve) that permits either zero flow (0%) or full flow (100%), and no other "in between" flow rate value, while nevertheless performing in the Split Flow mode of operation that is described above in conjunction with FIG. 4. The enhanced performance of the Split Flow mode is primarily due to the additional gas flow that travels to the GC 80, via the gas that travels through the flow control valve 100 from the Helium input device at 50. The amount of gas flow through the passageway 66 could be regulated (if necessary) by another method than use of a proportional valve for PV1.

Figure 5:
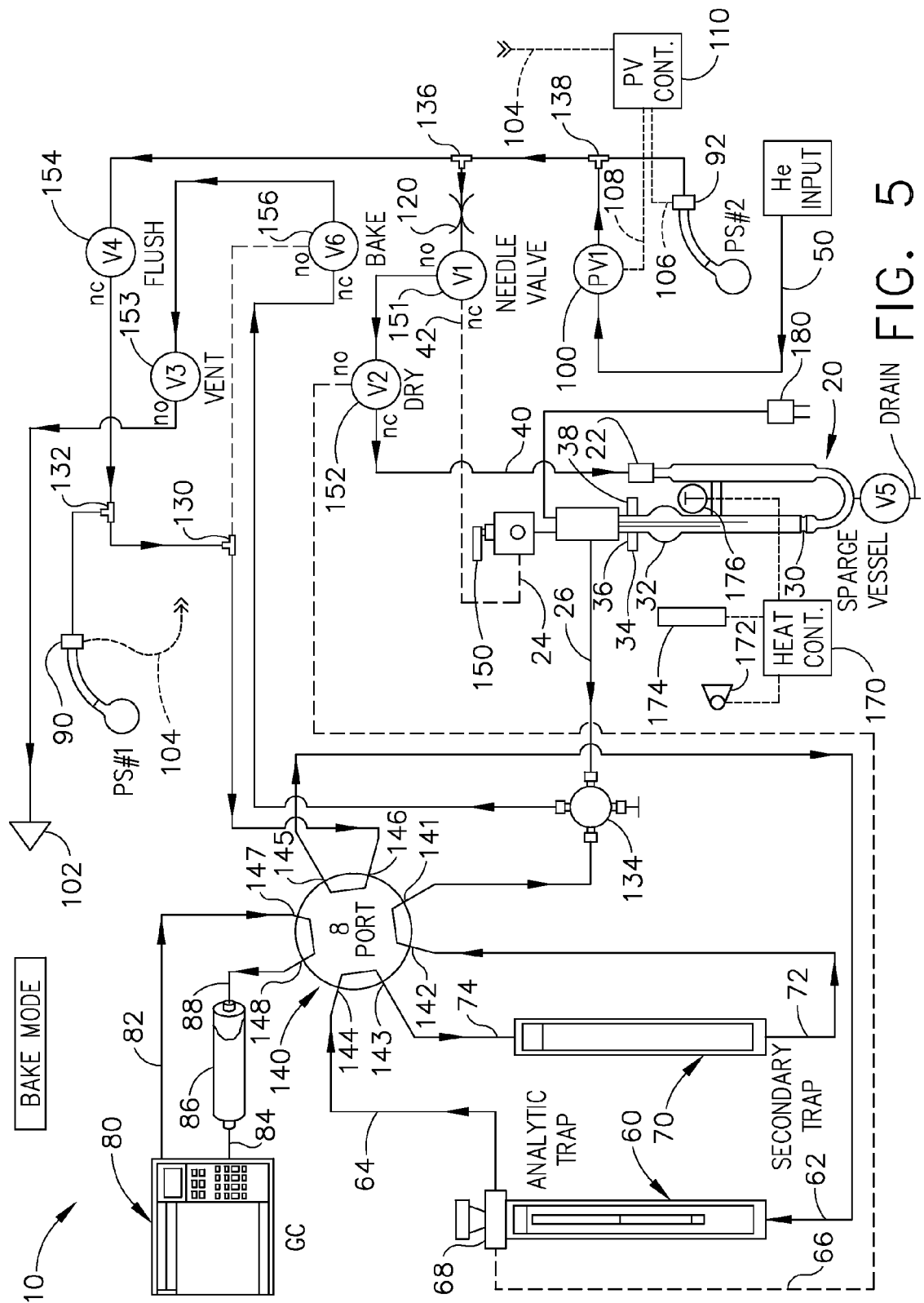
FIG. 5 is a fluidic schematic diagram of the purge and trap concentrator system of FIG. 1A, showing the system in an operating mode called "Bake Mode."

Referring now to FIG. 5, the system 10 is illustrated as it would be configured for a "Bake Mode" (or "bake procedure"). During this Bake Mode, the temperature of the sparge vessel is controlled by use of the heater controller 170, which controls the fan/blower 172 and also controls the magnitude of current through the resistive heating elements 174. Because of the fan's air flow, and using ductwork to direct this air flow, the thermal energy from the heating elements 174 is thereby forced by thermal convection to the sample portion 28 of the sparge vessel 20. This will tend to clean the surfaces of the sparge vessel, while the bake temperature can be precisely controlled, generally using a P-I-D algorithm for controlling the sparge vessel heater temperature. The actual temperature is detected by a temperature sensor 176, which typically can be a thermocouple, or some other type of metallic transducer, such as a resistance temperature detector made of platinum (also referred to as a "RTD").

During the Bake Mode, the Dry Purge Valve 152, and the Backflush Valve 154 are turned ON, along with the Bake Valve 156. The Vent Valve 153 is OFF, which allows gas flow through it normally-open port. The eight-port valve is set to its Position A. The proportional valve 100 is now controlled to a "bake flow" setpoint by the PV controller 110.

Figure 11:
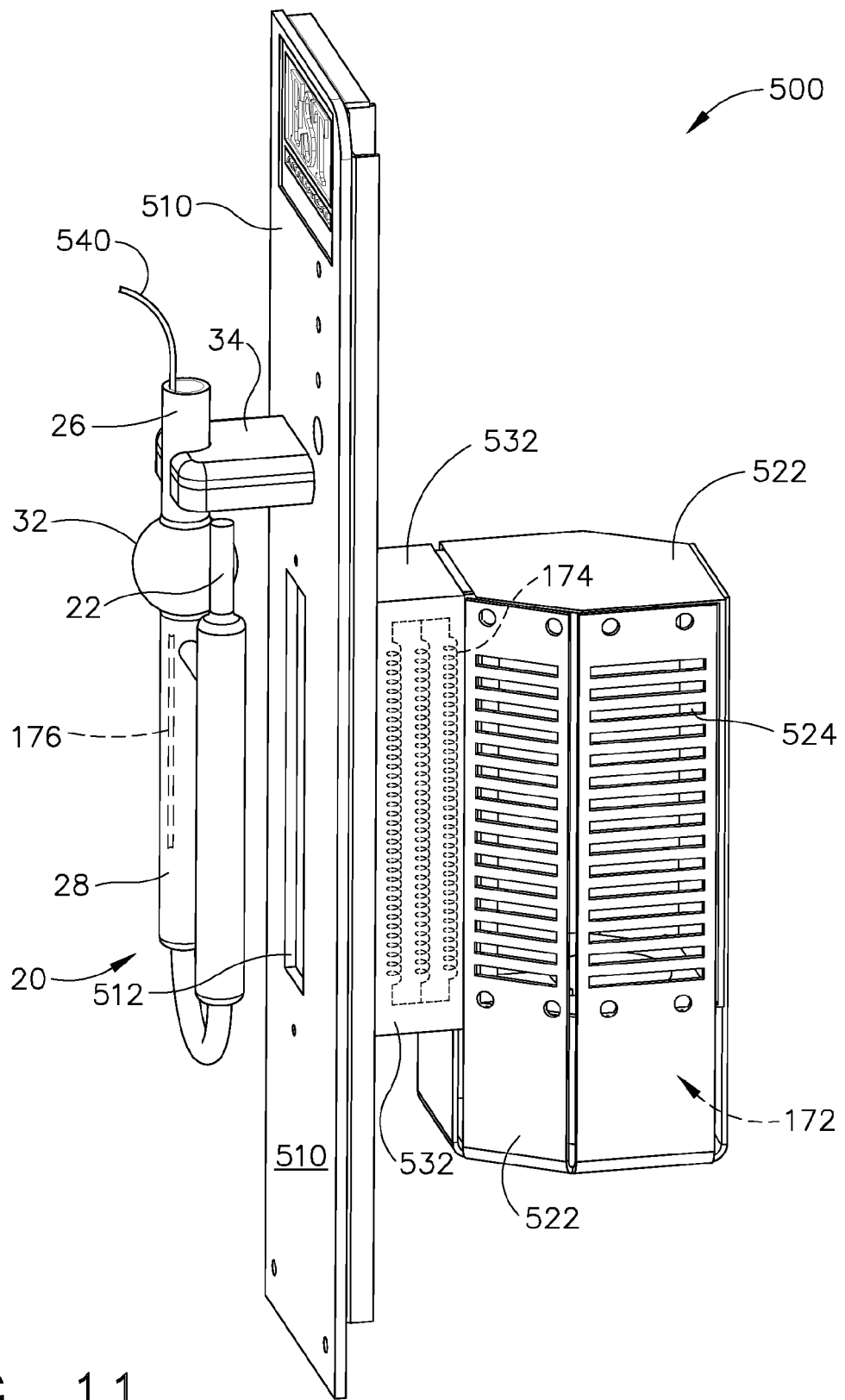
FIG. 11 is a perspective view of a portion of the purge and trap concentrator system of the present invention, showing the sparge vessel and the temperature control system used with the sparge vessel that heats and cools the sparge vessel, under control of a system heating controller.

Referring now to FIG. 11, the sparge vessel area is depicted as being mounted on a mounting plate 510, in which the sparge vessel 20 has its foam sensor (i.e., the sensing subassembly 34) surrounding the outlet portion 26 of the sparge vessel. As discussed above, the foam sensor has a fiber optic cable that directs light through the sparge vessel, and an optical sensor on the opposite side of the sparge vessel outlet 26 to receive that light if no foaming is occurring. If foaming occurs to a sufficient extent, then the foam bubbles will tend to interfere with the reception of the light on the optical sensor side of the detector; a "high level" of liquid at sensor 34 will also interfere with the reception of light. By use of this arrangement, the foam sensor 34 acts as both an overfill sensor and a foam detection sensor, using a single optical sensing device 38.

The foam sensor 34 includes the termination end of the fiber optic cable 36, which emits electromagnetic energy at a predetermined wavelength, such as a visible light wavelength or an infrared wavelength. The fiber optic cable acts as an optical waveguide, and it has an opposite "receiving" end that is optically coupled to a light source, such as a light emitting diode (LED) or a laser diode, for example. The system controller (e.g., the "heater controller" 170) includes a signal generator that can adjust the magnitude of the optical energy that is emitted by the light source, if desired. The signal generator also can cause the light source to emit pulses of electromagnetic energy, if desired. The optical sensor 38 essentially can be any form of transducer that responds to electromagnetic energy (e.g., photons), and the most common forms used are a photodiode or a phototransistor, with appropriate biasing electrical components. This includes photovoltaic cells, for example.

The heater subassembly is generally depicted by the reference numeral 500 on FIG. 11. The blower (or fan) is at reference numeral 172, and is contained inside a ducting or ventilating conduit area by ducting 522, with certain ventilation slots 524. The heating elements 174 are contained within a secondary ducting arrangement at 532. When the fan is turning, air will be forced through the ducting 522 and into the ducting area 532 where the heating elements 174 are positioned. In this manner, the heating elements 174 act as a radiant heater within the ducting area 532, and the moving air thus heated will then pass through a slot 512 in the mounting plate 510 and be directed to the sample portion 28 of the sparge vessel 20. This effectively heats the sparge vessel sample portion 28 by thermal convection. This ducting arrangement can also be referred to as a "ductwork subassembly."

It will be understood that electrical conductors or "leads" will be necessary for the fan 172 and the resistive heating elements 174. These electrical leads are not illustrated in FIG. 11, for purposes of clarity. The same is true for the fiber optic cables that extend into the foam sensor 34; there will be such cables extending through the mounting plate 510 to the right (on FIG. 11), but those cables are not depicted on FIG. 11 for the purposes of clarity. The electrical lead to the temperature sensor is depicted at reference numeral 540 on FIG. 11, and the extension to the temperature sensor itself is at 176.

At the end of the bake cycle, it is desirable to quickly cool the sparge vessel. The present invention does so by blowing cool air via the fan 172, while the heating elements 174 are de-energized. This will quickly cool the sparge vessel 20, and it is possible to cool the sparge vessel from a bake temperature setpoint to a purge temperature setpoint in less than ninety seconds, thereby enabling the system 10 to quickly begin a new sampling cycle.

Before a desorption step begins, the purge and trap system of the present invention may also be configured to pressurize the "dead volume" involving the eight-port valve 140 and the input to the GC instrument 80. This dead volume includes the passageway 62, at the "bottom" of the analytic trap 60, and sometimes may include the passageway 64 between the trap 60 and the port 144 of the eight-port valve 140.

As noted above, in conventional purge and trap systems, the dead volume is not pressurized by the purge and trap system before the analyzer trap is heated, and before the GC's carrier gas begins to flow through these passageways 62 and 64. When the GC instrument's pressurized carrier gas is "switched" into the passageway 62 by the eight-port valve (through the analyzer trap 60), a sudden pressure increase occurs which can cause the problems discussed above.

The present invention uses a pressure control valve (e.g., the proportional valve 100) to create a pressure in the passageway 62 at the "bottom" of the trap 60, preferably before the trap begins to be heated and before the desorbtion step begins. This pressure is referred to herein as the "desorbtion pressure control," or "DPC" pressure. The DPC pressure is controlled by the PV controller 110, and uses a pressure sensor 92 to provide a feedback control signal that indicates the actual system pressure in real time at the output side of the pressure control valve 100. As the DPC pressure is built up, the PV controller 110 will decrease the gas flow through the pressure control valve 100, so that the desired DPC pressure is substantially maintained. If the pressure control valve 100 is a proportional valve (or some other type of variable output pressure or variable flow valve), then the PV controller will be able to directly control the system pressure based on the feedback signal from pressure sensor 92. If the gas flow rate essentially falls to zero while maintained the DPC pressure, then the system will be "deadheaded," and the pressure everywhere in the system passageways will be substantially equal to the pressure at the sensor 92, since there will be no pressure losses at "no flow."

The DPC pressure in the system at the trap 60 may be built up at the end of a dry purge mode, for example, by closing the vent 102 (e.g., by using the vent valve 153), and then ramping the pressure from near zero to the desired DPC pressure. By building a pressure in the system at the trap 60, the passageway at 62 will not experience a sudden pressure increase when the eight-port valve 140 cycles (changes state) from its position A to position B. This provides an improvement in the transfer rate and in the analytical resolution of the extracted VOCs; also it reduces or eliminates moisture from being transferred to the GC instrument 80 when sampling an aqueous sample matrix, which would otherwise affect the analytical resolution and detected recovery of the extracted VOCs.

The DPC pressure setpoint can be selected by a user, by entering data on a user interface that communicates commands to the system controller. This is discussed in greater detail below, in the discussion of the flow charts. The software executed by the system controller will typically contain a default pressure value for the DPC pressure setpoint.

It will be understood that the desorption pressure control feature of the present invention can be used with either the "split mode" desorption cycle of FIG. 4, or the "normal mode" desorption cycle of FIG. 3.

Discussion of Flow Charts

Figure 6:
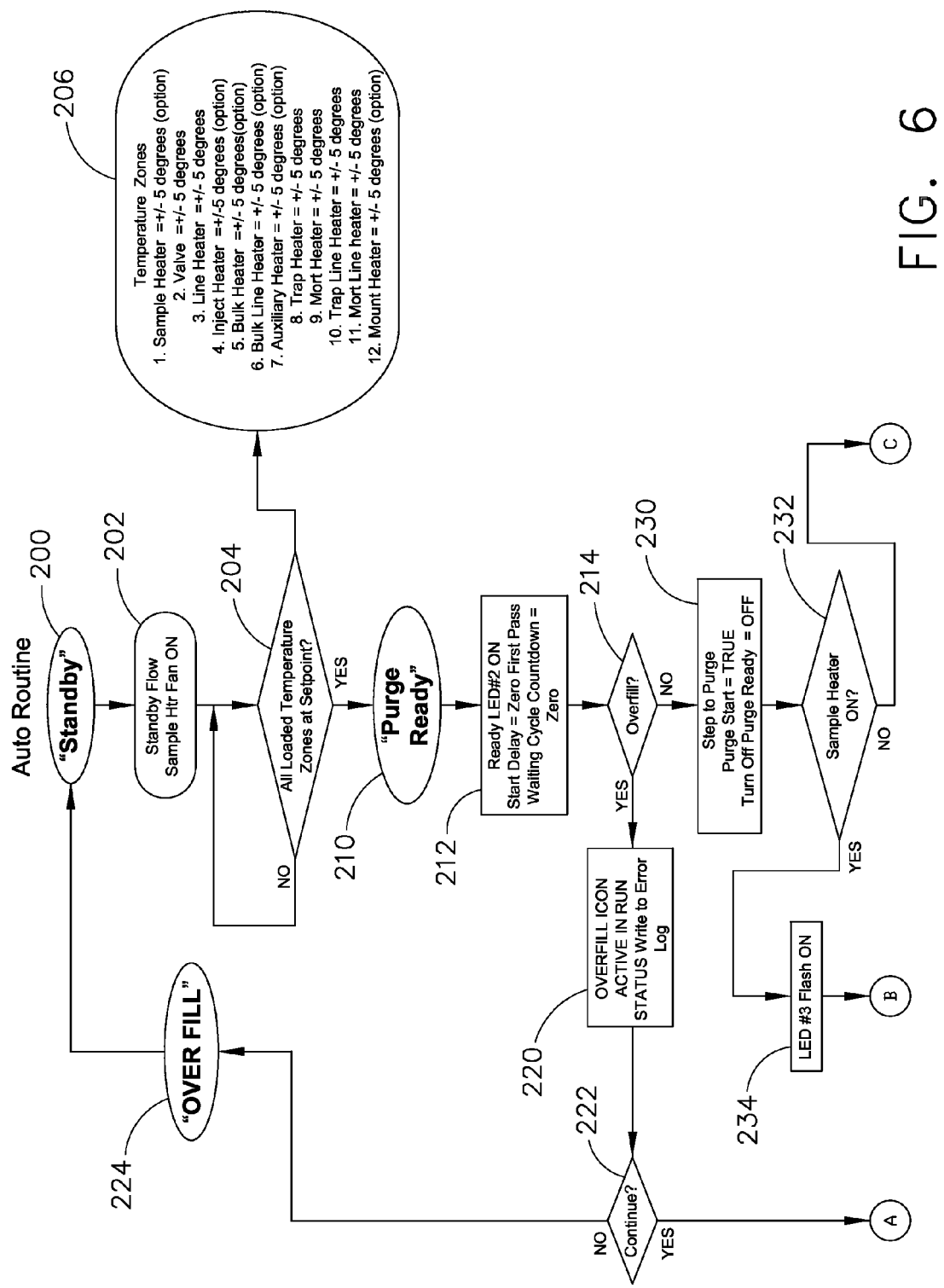
FIG. 6 is a flow chart showing some of the logical steps used for controlling some of the various operating modes of the present invention, including the initial operating modes for "Standby" and "Purge Ready."

Referring now to FIG. 6, the beginning of a flow chart showing some of the important steps in an automatic controller routine are illustrated. Starting with a "Standby" mode at 200 (which is displayed on a computer monitor screen), a step 202 turns ON the sample heater fan 172 and also begins the standby flow of helium gases. Along with the fan (or blower) 172, the heat controller 170 also will energize the electrical heating elements at 174. This will begin to raise the temperature of any sample now in the sparge vessel 20.

A decision step 204 is executed next, and it determines if all of the "loaded" temperature zones are currently at their setpoints. These temperature zones are described at step 206 on the flow chart of FIG. 6. As can be seen in the illustrated example of the present invention, there are twelve different heating temperature zones, and each one can have a different temperature setpoint value and a different temperature tolerance if desired. If all of the temperature zones are not at their setpoint (within their correct tolerance), then the logic flow travels from the NO output back to the top of decision step 204 until all of the zones are within their predetermined tolerances of the setpoint temperatures. After that occurs, the logic flow arrives at a "Purge Ready" mode at a step 210, which displays this status on the computer monitor.

A step 212 now turns on the "ready" indicator light (so the user can see that the Purge Ready mode has occurred), and starts a time delay for a "first pass" of delay in the purge cycle. The "waiting" cycle begins a countdown until it reaches zero (0), at a step 212.

A decision step 214 now determines whether or not there has been an overfill within the sparge vessel. If not, then a step 230 begins the process of stepping to the purge mode. Step 230 determines if the Purge Start input has been activated, and if so, the controller will turn off the Purge Ready indicator message. As the system is waiting to "Step to Purge," it is waiting for an input. This could be a manual input at the operator display control panel, or it could be an automatic input based upon an external signal received as an input by the controller. A decision step 232 now determines whether or not the sample heater is still on, and if not, the logic flow travels to a step 252 that turns on the "Purge" indicator message, and the system now has entered the "Purge" mode at 250.

Referring back to decision step 214, if an overfill condition exists, then a step 220 will display the overfill icon on the computer screen, and will write to an Error Log, in which the entry will state that the overfill was active in a run status. A decision step 222 now determines whether or not the system should continue toward the purge mode. This is an input that the user controls, and if the user enters a NO input, then the logic flow is briefly directed to an "Overfill" mode display message at 224, and the logic flow is directed back to the Standby mode at 200. On the other hand, if the user wishes to continue, then the logic flow is directed out the YES output from step 222, and this logic flow travels to a letter "A" that is further directed to FIG. 8, and will be discussed below.

Figure 7:
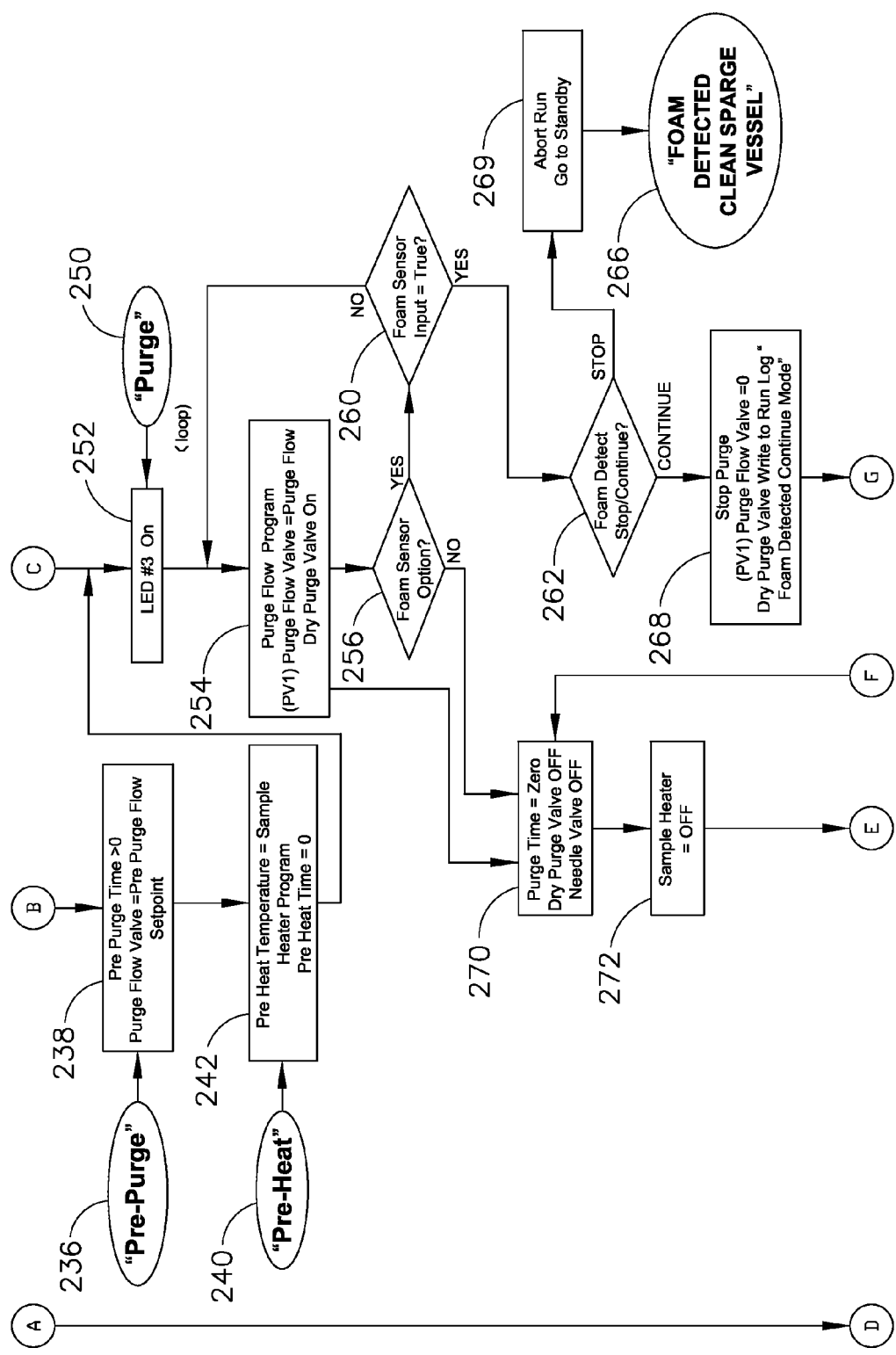
FIG. 7 is a second flow chart showing some of the logical steps used for controlling some of the operating modes of the present invention, including the "Purge" mode.

At decision step 232, if the sample heater is still ON, the indicating light #3 will begin flashing at a step 234. The logic flow is then directed to a step 238 (see FIG. 7) in which the status is checked to see if the pre-purge time is greater than zero (0), and also the purge flow valve 100 (which is the proportional valve PV1) will now be controlled using the pre-purge flow setpoint value. This is also referred to as the "Pre-Purge" mode at 236 on FIG. 7, which displays this status on the computer monitor.

Once the conditions at step 238 have been satisfied, the logic flow is directed to a step 242 in which the preheat temperature is set to be the sample heater program temperature, and the preheat time is set equal to zero (0). This is also referred to as the "Pre-Heat" mode at 240 which is displayed. The logic flow is now directed to step 252, in which the system enters the "Purge" mode 250, which is displayed.

Once the Purge mode has been entered, a step 254 begins the purge flow program. (This is Purge Mode "A," as illustrated on FIG. 1A. The purge flow valve 100 (proportional valve PV1) is set to control using the purge flow control setpoint value. The Dry Purge Valve is also turned ON (this is valve V2 at 152). A decision step 256 now determines whether or not the "foam sensor option" has been selected by the user. If YES, then a decision step 260 determines whether or not the foam sensor input is now active. If not, then the logic flow is directed back to the purge flow program at step 254. On the other hand, if the foam sensor input is active, the logic flow is directed to a decision step 262 that determines whether or not the foam detect selection option has been placed into the "STOP" mode or the "CONTINUE" mode. If the STOP mode has been selected (by the user), then a step 264 aborts this sample run, and the logic flow goes back to the Standby mode, and a message is displayed (on the system monitor) at a step 266 that foam has been detected and that the sparge vessel should be cleaned.

At step 262, if the CONTINUE selection has been entered, then a step 268 stops the purge cycle, and sets the purge flow valve 100 (PV1) to a value of zero (0), which stops the purge flow. The Dry Purge Valve 152 (V2) is turned OFF, and an entry is written to the Run Log that foam has been detected, in the CONTINUE mode. The logic flow is then directed to a decision step 290 on FIG. 8, through the letter "G," which will be discussed below.

If the foam sensor option has not been selected by the user at decision step 256, the logic flow is directed to a step 270 in which the purge time is set to zero (0), the Dry Purge Valve 152 (V2) is turned OFF, and the Needle Valve 151 (V1) is also turned OFF. A step 272 now turns the sample heater OFF, and the logic flow is then directed to a Dry Purge mode through the letter "E" and to FIG. 8 (discussed below).

Figure 8:
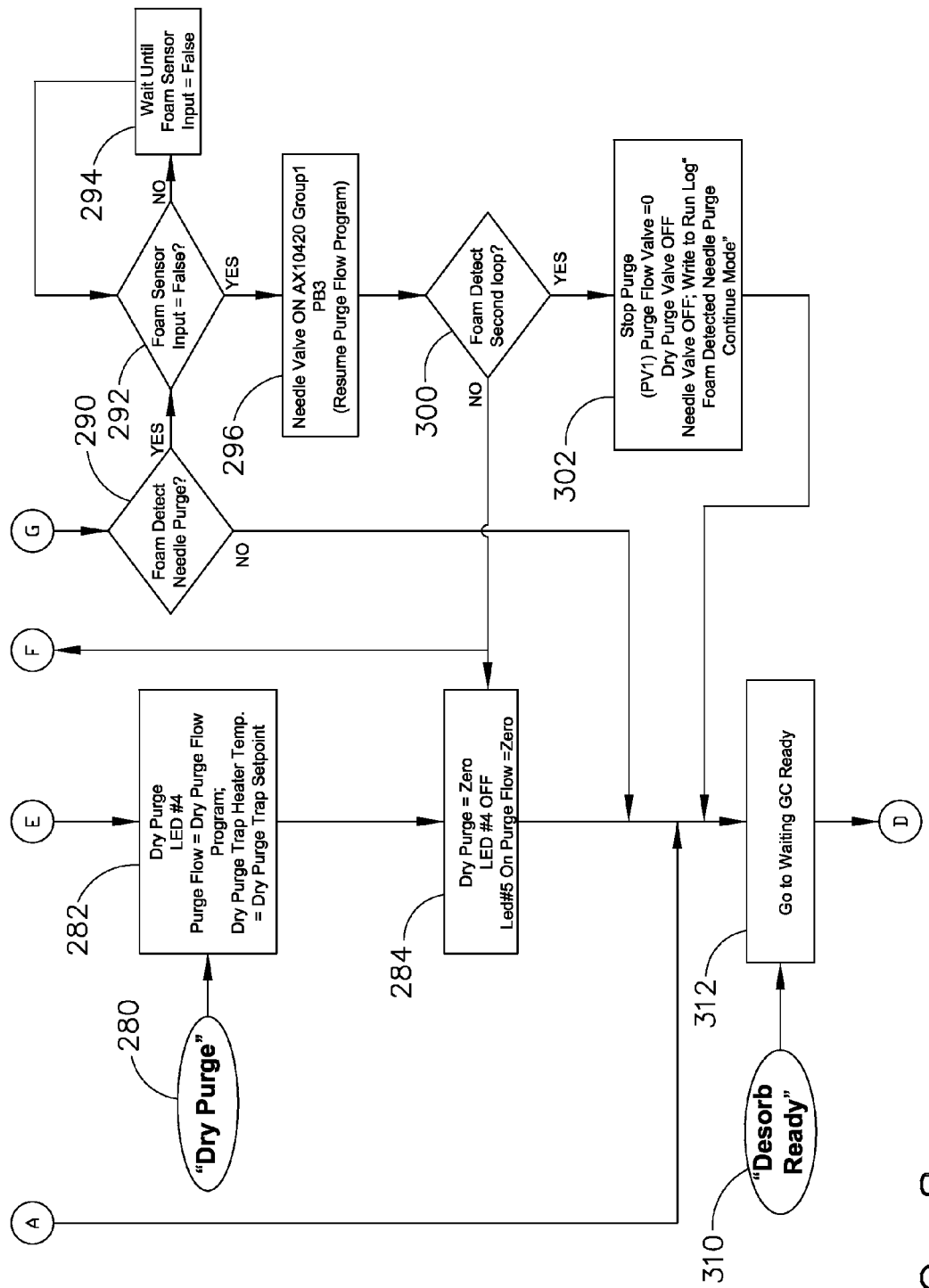
FIG. 8 is a third flow chart showing some of the logical steps used for controlling some of the operating modes of the present invention, including the "Dry Purge" mode.

Referring now to FIG. 8, the logic flow through letter "E" is directed to a step 282 which begins the "Dry Purge" mode at 280, which is displayed. An indicator light is also turned ON to inform the user that the Dry Purge mode has been entered. The purge flow valve 100 (PV1) is now set to run using the dry purge flow program setpoint.

Each of the traps 60 and 70 have their own heater and their own heater setpoint. The dry purge trap heater controller 170 is now set to the dry purge trap setpoint, which is an entry that can be controlled by the user (but also has a default, or suggested setpoint temperature). The trap pressure can be controlled by the pressure control valve 100 (PV1) prior to thermal heating of the adsorbent trap 60.

The logic flow is now directed to a step 284 that sets the dry purge timer to zero (0), and turns off the dry purge indicator light. Another indicator light is turned ON, and the purge flow is set to zero (0). Once the Dry Purge mode has been completed, the logic flow is directed to a step 212 that waits until the GC 80 (the gas chromatograph) is ready. This is the "Desorb Ready" mode at 210, which is displayed.

The logic flow entering FIG. 8 through letter "G" is directed to a decision step 290 in which it is determined if the foam detect system using the Needle Valve 151 (V1) needs to activate to run in the Purge Mode B, illustrated in FIG. 1B. If the answer is NO, then the logic flow is directed to the Desorb Ready step at 312. On the other hand, if the answer is YES, then a decision step 292 determines whether or not the foam sensor input is active or not. If it is not active, then the Needle Valve 151 (V1) is turned ON at a step 296. The purge flow program is resumed (in Mode B). On the other hand, if the foam sensor input is not false (meaning the foam sensor is active), then a step 294 causes the system to wait until the foam sensor input reads false (which means there is no foam at this time). A Wait step 294 essentially loops back to the beginning of the decision step 292, where the foam sensor input is again inspected.

From step 296, a decision step 300 determines if the foam detect algorithm has now entered its second loop. If the answer is NO, then the Dry Purge cycle is completed at step 284, and the Desorb Ready mode is entered at 312. If the second loop is active at step 300, then a step 302 stops the purge, and sets the purge flow valve 100 (PV1) to zero (0), turns the Dry Purge Valve 152 (V2) OFF, turns the Needle Valve 151 (V1) OFF, and writes an entry to the Run Log. This entry will state that foam was detected at the "Needle Valve Purge Continue" mode (i.e., Purge Mode B on FIG. 1B). When this occurs, the purge gas is thereby re-routed (during the foam detect second loop).

The logic flow now is directed to the Desorb Ready mode at step 312. The logic flow from letter "A" also is directed to the Desorb Ready step 312. From this step, the logic flow is directed to FIG. 9 through the letter "D." The "Desorb Ready" status is displayed at step 310.

Figure 9:
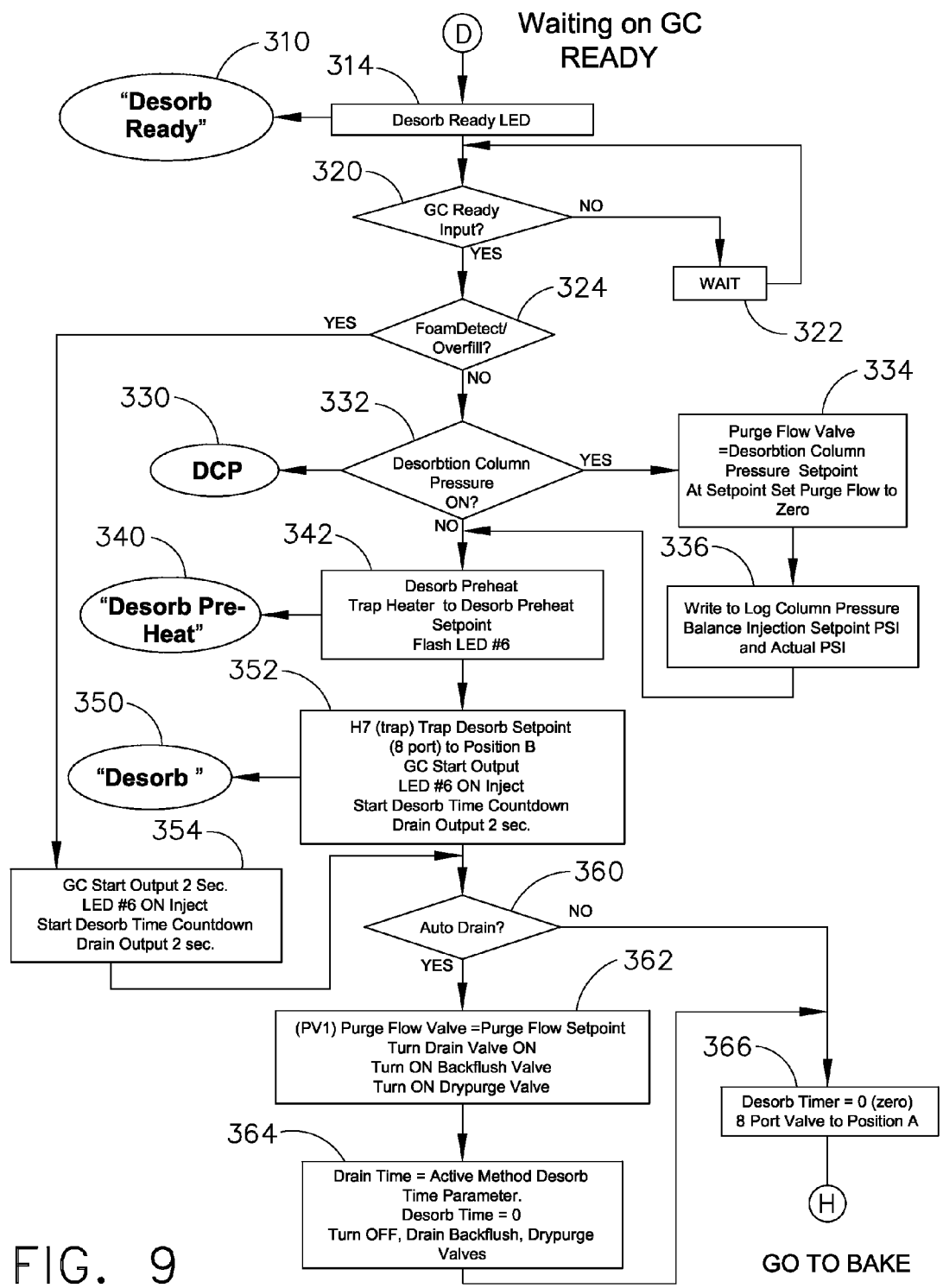
FIG. 9 is a fourth flow chart showing some of the logical steps used for controlling some of the operating modes of the present invention, including the "Desorb Ready" and the beginning of the "Desorb" mode.

On FIG. 9, the system is now waiting for the gas chromatograph to become "Ready." This is the Desorb Ready mode 310, which is displayed. While the system is at the Desorb Ready Mode 310, at the logic step 314 the system is waiting for an input. Again, this input could be a manual entry by person at the operator display control panel of the system controller, or it could be an external signal received as an input by the controller. At a step 312, the Desorb Ready status is also made apparent to the user by turning on an indicator light.

From step 312, a decision step 320 now determines whether or not the gas chromatograph input indicates that it is ready, and if not a Wait step 322 loops the logic flow back to the beginning of decision step 320. Once the GC is actually ready and the input is received at step 320, then the logic flow travels out the YES output to a decision step 324. The purpose of decision step 324 is to detect whether a foaming condition or an overfill occurred earlier for this sample; again the foam detector is now inspected. If the answer is YES, then the logic flow is directed to a step 354 that delays the GC start for two seconds and turns on an indicator light for the Inject mode.

If the logic flow reaches step 354, then the concentrated sample in the trap will be discarded and not sent to the GC 80. The desorb timer is started, and a delay of two seconds is imposed before turning on the Drain Valve (V5) output. The logic flow is then directed to a decision step 360 where it is determined whether the automatic drain function has been selected.

Back at decision step 324, if there is no detection of an overfill, then the logic flow is directed to a decision step 332 that determines if the desorbtion column pressure is now ON. This is the "DCP" mode 330, which is displayed. If the answer is YES, then a step 334 controls the purge flow valve 100 (PV1) to the desorbtion column pressure setpoint. The proportional valve 100 is set to a "Desorbtion Column Pressure Setpoint." Once the setpoint pressure is reached, the purge flow is set to zero (0), using proportional valve PV1, and then no appreciable flow will be output from the valve 100. A step 336 now writes to the log a message that the column pressure balance injection setpoint pressure is at a particular (current) control setpoint in PSI, and also writes the actual pressure in PSI units to the log. The logic flow is now directed to a step 342.

If the desorbtion column pressure mode was turned OFF at step 332, then the logic flow is also directed to step 342. The system is now entering the "Desorb Pre-Heat" mode 340, which is displayed. In the Desorb Pre-Heat mode at step 342, the trap heater is set to the Desorb Pre-Heat setpoint. An indicator light is now flashed to inform the user of this status. A step 352 now sets the analytic trap 60 to the Desorb setpoint, and it sets the eight-port valve 140 to its "Position B." (See the flow diagram of FIG. 3 for this configuration.)

The trap 60 is now instructed to use its heater at a desorb temperature setpoint by the first instruction in step 352. After eight-port valve 140 is set to Position B, an electrical signal is sent to the GC 80 instructing it to start its run, since the purge and trap system has just injected a sample. The gas chromatograph 80 starts outputting its gas supply, and the indicator light that was flashing in step 342 is now turned ON continuously, to indicate that the GC injection has begun.

The last instruction in step 352 is a signal to an external device (such as an autosampler) to actuate its drain, and this signal is also referred to as a "drain signal" being sent from the purge and trap system. A desorb timer is started, and its countdown "timeout" to a drain output is two seconds (in this embodiment). This is the Desorb mode 350 (which is displayed on the User Controller), and in an optional mode of the present invention, the pressure control valve 100 (PV1) can be set to a "Split Flow" rate, which will be discussed in greater detail below. This is the mode that was discussed above in reference to FIG. 4, and is an enhancement provided by the present invention. In this "Desorbtion Split Flow Mode," the proportional valve 100 is now set to operate at the "Desorbtion Split Flow Rate," and the flow passageways will be used as depicted on FIG. 4.

The logic flow has now reached a decision step 360, where it is determined if an automatic drain function should be performed, and if not, a step 366 sets the desorb timer to zero (0) and moves the eight-port valve 140 back to Position A (which is the position illustrated in FIG. 2).

If the automatic drain function is to be used, then a step 362 controls the purge flow valve 100 (PV1) so that it controls from the purge flow setpoint. The Drain Valve (V5) is turned ON, the Backflush Valve 154 (V4) is turned ON, and the Dry Purge Valve 152 (V2) is turned ON. A step 364 determines if the drain time has reached the active desorb time parameter, and also determines if the desorb time has reached zero (0). If so, the Drain Valve (V5), Backflush Valve (V4), and Dry Purge Valve (V2), are all turned OFF. The logic flow is now directed to step 366 where the desorb timer is set to zero (0) and the eight-port valve is set to Position A. The logic flow is now directed to the "Bake" mode through the letter "H."

Figure 10:
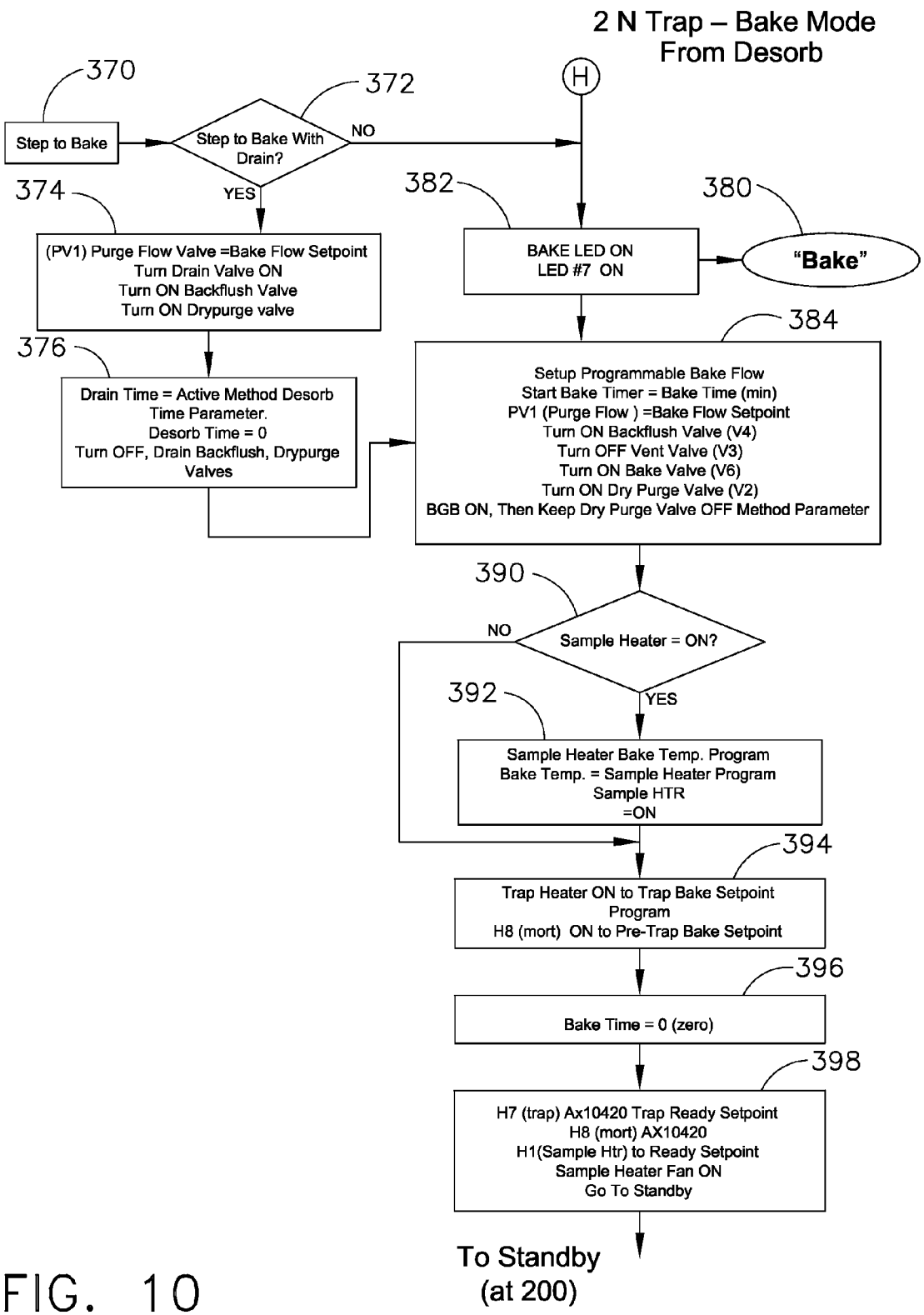
FIG. 10 is a fifth flow chart showing some of the logical steps used for controlling some of the operating modes of the present invention, including the "Bake" mode.

Referring now to FIG. 10, the system is about to reach the Bake mode. A step 370 can be activated such that the user may manually command the system to enter the Bake mode ("Step to Bake"), by a user input. A decision step 372 will determine whether or not the system should step to the Bake mode with the drain activated. If the answer is NO, then the logic flow is directed to step 382 and the Bake indicator light is turned ON. This is now the "Bake" mode 380, which is displayed on the user monitor screen.

In the Bake mode, the sparge vessel 20 receives a rinsing liquid, and also receives a "bake gas," which will tend to clean the glassware in preparation of receiving a new chemical sample at the sparge vessel. The system controller provides electrical signals to cause these steps to occur. In addition, the rinsing liquid can then be removed from the sparge vessel, again under the control of the system controller and its electrical signals.

If the Bake mode with drain is to be used, the logic flow is directed from step 372 to a step 374 in which the purge flow valve 100 (PV1) is set to control from the bake flow setpoint. The Drain Valve (V5) is turned ON, the Backflush Valve 154 (V4) is turned ON, and the Dry Purge Valve 152 (V2) is turned ON. As the Bake mode is running, a step 376 now determines if the drain time has reached the active desorb time parameter, and also will set the desorb time to zero once that has been accomplished. The Drain Valve (V5), Backflush Valve (V4), and Dry Purge Valve (V2) are all turned OFF. The logic flow is now directed to a step 384. This step 384 is also encountered from step 382.

At step 384, many things occur: the bake mode begins by setting up a programmable bake flow, and a Start Bake timer is initiated to be set to a bake time (in minutes) that can be controlled by the user (there is a suggested or default value). The purge flow valve 100 (PV1) is set to control from the bake flow setpoint. The Backflush Valve 154 (V4) is turned ON, the Vent Valve 153 (V3) is turned ON, the Bake Valve 156 (V6) is turned ON, and the Dry Purge Valve 152 (V2) is turned ON. Also, step 384 determines if the bake gas bypass mode is turned ON, and if so, flow to the sparge vessel is bypassed. This is accomplished by keeping the Dry Purge Valve 152 (V2) turned OFF.

The bottom instruction of step 384 can use a "Bake Gas Bypass Mode," if desired by the user. In that situation, the needle valve 151 (V1) is turned ON, and the Dry Purge valve 152 (V2) is turned OFF. This will re-direct the gas flow so that it travels along the passageway 42 and 24 to the upper portion of the "sample portion" of the sparge vessel, and then out the sparge vessel's outlet passageway 26. This will effectively bypass the sparge vessel during the bake mode, if desired. This is an alternative mode, and this bypass gas flow mode is not illustrated on FIG. 5.

A decision step 390 now determines if the sample heater is turned ON. If not, the logic flow is directed to a step 394. If so, a step 392 controls the sample heater to a bake temperature program, and the sample heater is turned ON. This includes both the blower (or fan) 172 and the resistive heating elements 174. The percentage output for the resistive wire heater could be all the way from 100% duty cycle all the way down to 0% duty cycle, if desired. This can be adjusted using binary numbers; with an 8-bit number, the resolution would be one part in 256, which is about one-quarter % precision. Of course, if a greater resolution is desired, then the controller can use larger binary numbers to control the duty cycle, such as 10-bit or 12-bit numbers (providing one part in 1024 for $\frac{1}{10}$% precision, or one part in 4096 for $\frac{1}{40}$% precision, respectively).

The blower fan speed can be controlled at a fairly wide range, depending upon the type of motor and blower fan being used. In one mode of the present invention, this range can be from full duty cycle (100%) down as low as 20% duty cycle. Of course, the blower motor can be completely turned off, if desired, depending upon whether or not the purge and trap system is going to be not used for fairly long periods of time. In addition, the blower fan's control signal can be varied in the range 0-100% if desired, even if the physical fan cannot slow all the way down to zero RPM, without actually turning it off. The blower fan can also be controlled using binary numbers of a predetermined resolution, such as with 8-bit, 10-bit, or 12-bit numbers. It will be understood that analog control techniques could be used instead of digital control techniques, if desired, in the present invention.

The first instruction at step 394 is for the trap 60, which is set to its particular bake temperature setpoint. The second instruction is for the other trap 70 (also referred to as the "pre-trap"), which is set to its particular bake temperature setpoint. Thus, at step 394 the trap heater is turned ON to the trap bake setpoint program. Also the temperature zone H8 is turned ON to the pre-trap bake setpoint. A step 396 determines if the bake time has reached zero (0), which means that the bake timer has timed out, and if so, a step 398 controls the analytic trap 60 temperature to the "Trap Ready" setpoint, and turns the sample heater 174 to its "Ready" setpoint value.

An optional feature of the present invention is to use multiple Bake cycles before proceeding to the next sampling procedure step, or before receiving the next chemical sample at the sparge vessel. This feature can be automatically implemented by a user selection, in which the user would enter (in advance) the number of Bake cycles that the purge and trap concentrator system 10 will undergo. Of course, the number of selected Bake cycles could be only one, which is the conventional method that has been used in the past. On the other hand, the present invention allows for a greater amount of "cleaning" of the glassware by providing additional Bake cycles, and this can be done automatically.

The present invention also provides greater flexibility in controlling the sparge vessel temperature during Bake cycles (or Bake "steps"). For example, an "initial" temperature setpoint is provided for selection by the user, which become the process control variable at the beginning of the Bake step. Then the temperature setpoint can be increased, and this temperature rise over time can be controlled as a "ramp" function, if desired; that is, the user can select a numeric ramp value in units of degrees vs. time. The initial temperature setpoint can be held for a selectable amount of time by the user (a "hold time" setpoint), before the temperature increase begins to take effect. Furthermore, the maximum Bake step temperature is selectable by the user, and if desired, a "final" sparge vessel temperature setpoint can be selected by the user, in which the final temperature may be different than the maximum Bake step temperature. Thus the sparge vessel temperature will follow a programmable temperature profile that begins with the controlled initial temperature (for a predetermined time period), then the controlled temperature rise (at a predetermined rate of increase), until reaching the maximum Bake temperature, which will be the control variable for most of the remainder of the Bake step; finally the controlled final Bake temperature will be used as the process control variable, at the terminal portion of the Bake step.

In step 398, the sample heater 174 is turned off, while the fan (or blower) 172 is turned on to its full 100% duty cycle. This is the "cooling mode" for the sparge vessel, in which the electrically controlled device (i.e., the fan) is also used to move air for removing thermal energy from the sparge vessel. The other instructions in this step 398 are to instruct the trap 60 and 70 to turn their heaters completely off, so as to also be in the "cooling mode." For example, the sparge vessel 20 could be heated to 85 degrees C. as the final sparge vessel temperature for a Bake step, and it is then quickly cooled to ambient temperature, within a fairly tight tolerance (such as ±5 degrees C.). For a given sampling application, the present invention can be designed so that the time to cool the sparge vessel does not inhibit the normal sample analysis cycle time for a purge and trap concentrator system.

As the sparge vessel 20 is cooled, the system is ready to go back to the standby mode (which is at step 200 on FIG. 6). This completes the cycle for a particular group of samples. On FIG. 10, The term "H8 (mort)" is a reference to a moisture reduction trap, as is the term "H7 (mort)." Such moisture reduction traps can be used as the traps 60 and 70 on FIG. 1A, for example.

It will be understood that the heater controller 170 and the proportional valve (PV1) controller 110 could be two separate control devices or they could be routines that are resident on a single process control computer. Such a process control computer could be a general purpose PC, using Microsoft WINDOWS as a graphic user interface, for example, or using UNIX or LINIX. A general purpose PC would preferably have a display monitor to show various equipment statuses, and/or a series of indicator lights (such as LED's) to show the status of the various modes used in the present invention. Any controller would typically include a processing circuit (e.g., a microprocessor or a logic state machine) and a memory circuit (e.g., RAM, ROM, EEPROM, etc.). In addition, it will be understood that the proportional valve controller 110 could operate using either analog or digital control techniques. If a digital controller is used, the valve control signal could be of 8-bit resolution, for example, which would provide a precision of one part in 256. A greater precision may well be desirable, and the valve control signal therefore use larger binary numbers, such as 10-bit numbers for one part in 1024 precision, or 12-bit numbers for one part in 4096 precision. Even greater precision is possible by using larger binary numbers for the control algorithms.

If a microprocessor or microcontroller (i.e., a "digital controller") is used as the proportional valve controller 110, then the binary signals that are calculated by the digital controller would typically be a relatively low voltage, low current electrical signal, such as a 0-5 VDC (or 4-20 mA) analog output signal from the digital controller. This assumes that the digital controller has some type of on-board Digital to Analog Converter (DAC). Otherwise, the digital controller could output a binary signal (either serial or parallel) to a separate DAC module, and that DAC module would output the low voltage, low current signal. Such a low power 0-5 VDC signal could not directly drive the proportional valve (PV1) 100, and so a driver module would typically be used to convert the low power signal to a more substantial (or "high power") signal. An exemplary driver module for this purpose is a Series B5950 proportional driver, sold by Canfield Connector of Youngstown, Ohio.

If a microprocessor or microcontroller (i.e., a "digital controller") is used as the heater controller 170, then the binary signals that are calculated by the digital controller would typically be a relatively low voltage, low current electrical signal, such as a 0-5 VDC analog output signal from the digital controller. This assumes that the digital controller has some type of on-board Digital to Analog Converter (DAC). Otherwise, the digital controller could output a binary signal (either serial or parallel) to a separate DAC module, and that DAC module would output the low voltage, low current signal. Such a low power 0-5 VDC signal could not directly drive the motor for the blower 172, and so a driver module would again typically be used to convert the low power signal to a more substantial (or "high power") signal. An exemplary driver module for this purpose is a model AX10415 analog output module, sold by AXIOM Technology Co., Ltd. in Taiwan; another exemplary driver module for this purpose is a model M3000 motion controller, sold by System Semiconductor, Inc., of Marlborough, Conn.

Two tables are provided below that summarize the use of the six solenoid valves and of the four-way valve 140 (i.e., the eight-port valve) for the various modes illustrated in the fluidic schematic diagrams and discussed above with respect to the logic flow chart. The first table shows the name of the system mode and the corresponding fluidic schematic drawing, and also shows the type of logic control setpoints that the proportional valve 100 will be using for the various operating modes. The second table again shows a listing of the mode in the left-hand column, and then lists the various modes or states of the solenoid valves, including the eight-port valve 140 and the six solenoid valves 151-156 (V1-V6). These tables are provided as follows:

TABLE #1

| Mode | Drawing | PURGE FLOW PV1 |
| --- | --- | --- |
| Purge A | FIG. 1A | Purge Flow |
| Purge B | FIG. 1B | Purge Flow |
| Standby/Dry Purge | FIG. 2 | Dry Purge Flow |
| Desorb - No Split | FIG. 3 | Desorb with Drain (PV = 0) |
| Desorb - With Split | FIG. 4 | Desorb Column Pressure |
| Bake | FIG. 5 | Bake Flow |
| BGB | FIG. 5* | BGB Flow |

TABLE #2

| Mode | 8-port | NEEDLE V1 | DRY V2 | VENT V3 | FLUSH V4 | DRAIN V5 | BAKE V6 |
| --- | --- | --- | --- | --- | --- | --- | --- |
| Purge A | A | OFF | ON | OFF | OFF | OFF | OFF |
| Purge B | A | ON | ON | OFF | OFF | OFF | OFF |
| Standby/Dry Purge | A | OFF | OFF | OFF | OFF | OFF | OFF |
| Desorb - No Split | B | ON | ON | ON | ON | ON | OFF |
| Desorb - With Split | B | OFF | OFF | ON | OFF | OFF | OFF |
| Bake | A | OFF | ON | OFF | ON | OFF | ON |
| BGB | A | ON | OFF | OFF | ON | OFF | ON |

The judicious use of the solenoid valves and the four-way valve 140 control the flow passageways for carrier gas, noble or inert gas through the proportional valve 100 (PV1), and the sample gases that run from the sparge vessel 20. These solenoid valves and the four-way valve also control the pathways of the gases that run through the traps, as well as what gases get vented (and to where) in a particular mode. It will be understood that the exact configurations depicted in the fluidic schematic diagrams of FIGS. 1A-5 could have certain alterations while still achieving the same effect, all without departing from the principles of the present invention.

It will be understood that the logical operations described in relation to the flow charts of FIGS. 6-10 can be implemented using sequential logic, such as by using microprocessor technology, or using a logic state machine, or perhaps by discrete logic; it even could be implemented using parallel processors. One preferred embodiment may use a microprocessor or microcontroller to execute software instructions that are stored in memory cells within an ASIC. In fact, the entire microprocessor, along with RAM and executable ROM, may be contained within a single ASIC, in one mode of the present invention. Of course, other types of circuitry could be used to implement these logical operations depicted in the drawings without departing from the principles of the present invention.

It will be further understood that the precise logical operations depicted in the flow charts of FIGS. 6-10, and discussed above, could be somewhat modified to perform similar, although not exact, functions without departing from the principles of the present invention. The exact nature of some of the decision steps and other commands in these flow charts are directed toward specific future models of chemical analyzer systems (those involving EST analyzers, for example) and certainly similar, but somewhat different, steps would be taken for use with other models or brands of chemical analyzer systems in many instances, with the overall inventive results being the same.

All documents cited in the Background of the Invention and in the Detailed Description of the Invention are, in relevant part, incorporated herein by reference; the citation of any document is not to be construed as an admission that it is prior art with respect to the present invention.

The foregoing description of a preferred embodiment of the invention has been presented for purposes of illustration and description. It is not intended to be exhaustive or to limit the invention to the precise form disclosed, and the present invention may be further modified within the spirit and scope of this disclosure. Any examples described or illustrated herein are intended as non-limiting examples, and many modifications or variations of the examples, or of the preferred embodiment(s), are possible in light of the above teachings, without departing from the spirit and scope of the present invention. The embodiment(s) was chosen and described in order to illustrate the principles of the invention and its practical application to thereby enable one of ordinary skill in the art to utilize the invention in various embodiments and with various modifications as are suited to particular uses contemplated. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A purge and trap concentrator system, comprising:
   (a) a system controller;
   (b) a first source of gas, which provides a first gas;
   (c) a plurality of fluidic control devices and a plurality of fluidic passages which fluidically connect said plurality of fluidic control devices;
   (d) a variable flow rate gas flow control valve that is controlled by a first signal from said system controller, said gas flow control valve having a first fluidic inlet and a first fluidic outlet which, under control of said first signal, acts to pass a gas flow therethrough, said first fluidic inlet being in fluidic communication with said source of gas and receiving said first gas, said first fluidic outlet dispensing a second gas when required by said first signal;

(e) an external instrument, which includes second source of gas that supplies a third gas, said external instrument having a second fluidic outlet that supplies said third gas, and a second fluidic inlet; and (f) an analytic trap, having:
   (i) a first trap port, a second trap port, and a third trap port; wherein:
      (A) said first trap port is selectively in fluidic communication with said first fluidic outlet of the gas flow control valve,
      (B) said second trap port is selectively in fluidic communication with a vent, through said plurality of fluidic control devices and plurality of fluidic passages, and is selectively in fluidic communication with said second fluidic output of the external instrument, through said plurality of fluidic control devices and plurality of fluidic passages, and
      (C) said third trap port is selectively in fluidic communication with said second inlet of said external instrument;
   (ii) a first chamber that is coupled to said second trap port, said first chamber being designed to receive a concentrated chemical sample, said first chamber acting to remove at least one predetermined substance from said concentrated chemical sample, and thereby create an "extracted sample gas flow";
   (iii) a second chamber that is coupled to said first chamber, to said first trap port, and to said third trap port; and (g) wherein, before a desorbtion procedure begins:
   (i) said plurality of fluidic control devices are in a first state;
   (ii) said second gas is received at said first trap port of the analytic trap, and flows into said first chamber;
   (iii) a fourth gas exits said first chamber at said second trap port, and flows toward a vent, through said plurality of fluidic control devices and plurality of fluidic passages, including a vent valve that is open at this time;
   (iv) then said vent valve is closed by a second signal from said system controller, and said fourth gas begins to build a desorbtion pressure control ("DPC") pressure at said second trap port, wherein said DPC pressure is controlled by said gas flow control valve, which is controlled by said first signal from said system controller; and
   (v) said DPC pressure reaches a predetermined magnitude; and (h) wherein, a desorbtion procedure begins, such that:
   (i) said plurality of fluidic control devices are activated into a second state, under the control of a third signal from said system controller;
   (ii) said third gas from the second outlet of the external instrument now flows to said second trap port and into said first chamber;
   (iii) said extracted sample gas flow travels from said first chamber into said second chamber; and
   (iv) a fifth gas flow, which includes said extracted sample gas flow, exits said second chamber at said third trap port and flows toward said second inlet of said external instrument, through said plurality of fluidic control devices and plurality of fluidic passages.

2. The purge and trap concentrator system of claim 1, further comprising a trap heater that is turned on after said DPC pressure reaches the predetermined magnitude.

3. The purge and trap concentrator system of claim 1, wherein said external instrument comprises a gas chromatograph analyzer.

4. The purge and trap concentrator system of claim 1, wherein said extracted sample gas flow removed from said concentrated chemical sample comprises volatile organic compositions (VOCs).

5. The purge and trap concentrator system of claim 1, wherein said plurality of fluidic control devices include a multi-port two-position valve, which:
   (a) before said desorbtion procedure begins, said multi-port two-position valve is at its first position; and
   (b) as said desorbtion procedure begins, said multi-port two-position valve is indexed to its second position, under the control of said third signal.

6. The purge and trap concentrator system of claim 5, further comprising a pressure sensor that outputs a fourth signal to said system controller, which measures a magnitude of said DPC pressure in real time; and
   wherein, said predetermined magnitude of the DPC pressure is controlled by a user-entered setpoint to the system controller, which allows said purge and trap concentrator system to undergo a smooth transition of pressure variation at said second trap port when said multi-port two-position valve indexes from its first position to its second position, and said third gas pressure is introduced to said second trap port.

7. The purge and trap concentrator system of claim 1, wherein said desorbtion procedure of part (h) operates in one of: (i) a split mode of operation; and (ii) a no-split mode of operation.

8. The purge and trap concentrator system of claim 7, wherein during said split mode of operation, said second gas flow is directed from said first outlet of the gas control flow valve to said first trap port of the analytic trap, and said second gas flow is combined at said second chamber with said extracted sample gas flow, thereby creating a larger overall said fifth gas flow that now becomes available for analysis by said external instrument.

9. The purge and trap concentrator system of claim 1, wherein said gas flow control valve said gas flow valve comprises a variable position valve that exhibits a "low flow" mode in which its output gas flow is at a minimum amount, a "full flow" mode in which its output gas flow is at a maximum amount, and a "proportional flow" mode in which its output gas flow is at a value between said minimum amount and said maximum amount, under control of said first signal.

10. The purge and trap concentrator system of claim 9, wherein said variable position valve receives said first gas through said first fluidic inlet from said source of gas and, under control of said system controller, said variable position valve outputs through said first fluidic outlet a percentage of said first gas that is determined by a present position of said variable position valve.

11. The purge and trap concentrator system of claim 9, wherein: (a) said low flow mode is a percentage of fluid flow that is substantially 0% of said maximum amount of fluid flow, (b) said full flow mode is a percentage of fluid flow that is substantially 100% of said maximum amount of fluid flow, and (c) said proportional flow mode is a percentage of fluid flow that varies between 0% and 100% of said maximum amount of fluid flow, through said variable position valve.

12. The purge and trap concentrator system of claim 9, wherein said variable position valve is controlled by an analog signal.

13. The purge and trap concentrator system of claim 9, wherein said system controller receives a closed loop feedback signal from a pressure sensor, and uses a P-I-D control routine to control said variable position valve.

14. The purge and trap concentrator system of claim 9, further comprising a driver module that receives a low power signal from said system controller, and generates a relatively high power signal that directly drives said variable position valve.

15. The purge and trap concentrator system of claim 9, wherein said variable position valve is controlled by a binary signal of multiple digits, thereby providing a large number of discrete possible positions.

16. The purge and trap concentrator system of claim 15, wherein said binary signal is one of: (a) 8-bit precision, providing 256 different possible positions between 0% flow and 100% flow, inclusive; (b) 10-bit precision, providing 1024 different possible positions between 0% flow and 100% flow, inclusive; and (c) 12-bit precision, providing 4096 different possible positions between 0% flow and 100% flow, inclusive.

* * * * *